US009954185B2

(12) United States Patent
Takaku et al.

(10) Patent No.: US 9,954,185 B2
(45) Date of Patent: Apr. 24, 2018

(54) ORGANIC THIN FILM TRANSISTOR, ORGANIC SEMICONDUCTOR THIN FILM, AND ORGANIC SEMICONDUCTOR MATERIAL

(71) Applicant: FUJIFILM Corporation, Tokyo (JP)

(72) Inventors: Koji Takaku, Kanagawa (JP); Yuki Hirai, Kanagawa (JP); Wataru Sotoyama, Kanagawa (JP); Masaru Kinoshita, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 214 days.

(21) Appl. No.: 14/815,269

(22) Filed: Jul. 31, 2015

(65) Prior Publication Data

US 2016/0035984 A1 Feb. 4, 2016

Related U.S. Application Data

(63) Continuation of application No. PCT/JP2014/052217, filed on Jan. 31, 2014.

(30) Foreign Application Priority Data

Jan. 31, 2013 (JP) .................................. 2013-017018
Jan. 30, 2014 (JP) .................................. 2014-015379

(51) Int. Cl.
*H01L 51/00* (2006.01)
*H01B 1/00* (2006.01)
(Continued)

(52) U.S. Cl.
CPC ........ *H01L 51/0072* (2013.01); *C07D 209/80* (2013.01); *C07D 409/04* (2013.01);
(Continued)

(58) Field of Classification Search
CPC .......... H01B 1/00; H01B 1/12; H01B 1/1221; C07D 209/00; C07D 209/56; H01L 51/0032; H01L 51/0052; H01L 51/0067
See application file for complete search history.

(56) References Cited

U.S. PATENT DOCUMENTS 4,519,937 A * 5/1985 Papir .................... C07D 261/20
252/500
4,579,679 A * 4/1986 Papir .................... C07D 261/20
252/500

(Continued)

FOREIGN PATENT DOCUMENTS

JP 2011-037854 A 2/2011
JP 2012-513459 A 6/2012
(Continued)

OTHER PUBLICATIONS

Notification of Transmittal of Translation of the International Preliminary Report on Patentability and Translation of Written Opinion of the International Searching Authority; PCT/JP2014/052217; dated Aug. 13, 2015.

(Continued)

*Primary Examiner* — Mark Kopec
(74) *Attorney, Agent, or Firm* — Studebaker & Brackett PC

(57) ABSTRACT

An organic thin film transistor containing a compound represented by the following formula in a semiconductor active layer has a high carrier mobility and a small change in the threshold voltage after repeated driving. Z represents a substituent having a length of 3.7 Å or less, and at least one of $R^1$ to $R^8$ represents -L-R wherein L represents alkylene, etc., and R represents alkyl, etc.

(Continued)

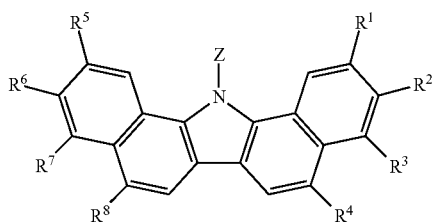

21 Claims, 2 Drawing Sheets

(51) Int. Cl.
    *H01B 1/12*     (2006.01)
    *C07D 209/80*     (2006.01)
    *C07D 409/04*     (2006.01)
    *C07D 409/14*     (2006.01)
    *H01L 51/05*     (2006.01)

(52) U.S. Cl.
    CPC ........... *C07D 409/14* (2013.01); *H01B 1/121* (2013.01); *H01L 51/0065* (2013.01); *H01L 51/0067* (2013.01); *H01L 51/0068* (2013.01); *H01L 51/0545* (2013.01); *H01L 51/0558* (2013.01)

(56) References Cited

U.S. PATENT DOCUMENTS

2011/0031484 A1     2/2011     Lee et al.
2011/0253944 A1     10/2011     Han et al.

FOREIGN PATENT DOCUMENTS

WO     2003/059014 A1     7/2003
WO     2010/114264 A2     10/2010

OTHER PUBLICATIONS

International Search Report and Written Opinion of the International Searching Authority; PCT/JP2014/052217; dated Mar. 11, 2014.

\* cited by examiner

ORGANIC THIN FILM TRANSISTOR, ORGANIC SEMICONDUCTOR THIN FILM, AND ORGANIC SEMICONDUCTOR MATERIAL

CROSS-REFERENCE TO RELATED APPLICATIONS

This application is a Continuation of PCT International Application No. PCT/JP2014/052217 filed on Jan. 31, 2014, which claims priority under 35 U.S.C. Section 119(a) to Japanese Patent Application No. 2013-017018 filed on Jan. 31, 2013, and Japanese Patent Application No. 2014-015379 filed on Jan. 30, 2014. Each of the above applications is hereby expressly incorporated by reference, in its entirety, into the present application.

BACKGROUND OF THE INVENTION

Field of the Invention

The present invention relates to an organic thin film transistor, an organic semiconductor thin film, and an organic semiconductor material. More specifically, the invention relates to a compound having a dibenzocarbazole structure, an organic thin film transistor containing the compound, an organic semiconductor material for a non-light emitting organic semiconductor device containing the compound, a material for an organic thin film transistor containing the compound, a coating solution for a non-light emitting organic semiconductor device containing the compound, and an organic semiconductor thin film for a non-light emitting organic semiconductor device containing the compound.

Background Art

A device using an organic semiconductor material is expected to have various advantages as compared to an ordinary device using an inorganic semiconductor material, such as silicon, and thus is receiving much attention. Examples of the device using an organic semiconductor material include a photoelectric conversion device, such as an organic thin film solar cell and a solid state image sensing device, using an organic semiconductor material as a photoelectric conversion material, and a non-light emitting organic transistor. The device using an organic semiconductor material has a possibility that a device having a large area may be produced at a low temperature and a low cost, as compared to a device using an inorganic semiconductor material. Furthermore, the characteristics of the material may be easily changed by changing the molecular structure thereof, and thus there is a wide range of variations in materials, by which functions and devices that have not been achieved by an inorganic semiconductor material may be realized.

For example, Patent Document 1 describes a compound having two dibenzocarbazole structures in the molecule, and describes that the compound may be used in a light emitting layer and a hole transporting layer of an organic electroluminescence (which may be referred to as organic EL), and the compound is excellent in heat resistance and has high Tg. However, Patent Document 1 does not describe or suggest the purpose of an organic transistor.

Patent Document 2 describes a compound having a dibenzocarbazole structure, and describes that the compound is an organic EL material having high efficiency and high durability. However, Patent Document 2 does not describe or suggest the purpose of an organic transistor.

Patent Document 3 describes as a compound having a dibenzocarbazole structure a dibenzocarbazole compound having a structure containing benzene rings condensed at two positions that are the most remote from the N atom of carbazole, as an organic semiconductor compound, and describes that the compound has high solubility in an organic solvent. Patent Document 3 describes that the organic semiconductor compound may be applied to various purposes, and describes that the compound may be applied to a thin film transistor (TFT), but the examples thereof disclose only the production of a solar cell but do not disclose the production of an organic thin film transistor.

Patent Document 4 does not clearly describe a compound having a dibenzocarbazole structure, but describes that a compound having a benzocarbazole structure may be used as an organic EL material, and describes that a low driving voltage, a high current density, a high efficiency, a high quantum efficiency and a high luminance are achieved.

CITATION LIST

Patent Documents

Patent Document 1: WO 2003/059014
Patent Document 2: WO 2010/114264
Patent Document 3: JP-A-2012-513459
Patent Document 4: JP-A-2011-37854

SUMMARY OF INVENTION

It has been known that a polycyclic condensed compound containing an aromatic heterocyclic ring is useful as a material for an organic EL device, as described in Patent Documents 1 and 2. However, it may not be said that a compound that is useful as a material for an organic EL device is immediately useful as a semiconductor material for an organic thin film transistor. This is because there is a difference in the characteristics demanded for the organic compound between an organic EL device and an organic thin film transistor. An organic EL device generally requires charge transport in the thickness direction of the thin film (which is generally from several nanometers to several hundred nanometers), whereas an organic thin film transistor requires charge (carrier) transport in a long distance between electrodes in the plane direction of the thin film (which is generally from several micrometers to several hundred micrometers). Accordingly, the demanded carrier mobility is considerably high. Thus, as a semiconductor material for an organic thin film transistor, an organic compound that has a high alignment order of molecules with high crystallinity is demanded. Furthermore, for achieving a high carrier mobility, the π-conjugate plane is preferably perpendicular to the substrate. In an organic EL device, on the other hand, a device that has a high light emission efficiency and uniform in-plane light emission is demanded for enhancing the light emission efficiency. In general, an organic compound having high crystallinity may be a cause of light emission defects, such as in-plane electric field unevenness, in-plane light emission unevenness and light emission quenching, and thus the material for an organic EL device is demanded to have high amorphous property with low crystallinity. Accordingly, even when an organic compound constituting a material for an organic EL device is diverted to an organic semiconductor material, good transistor characteristics may not immediately obtained.

Actually, the present inventors actually apply the polycyclic condensed compound in Patent Document 2 having an aromatic heterocyclic ring applied to an organic EL device to an organic thin film transistor, but it has been found that there is a problem that sufficient transistor characteristics are not obtained. Specifically, in the case where the compounds that are described with specific structures thereof in Patent Document 2 are applied as an organic semiconductor material to an organic thin film transistor, the investigations made by the inventors reveal that a high carrier mobility is not obtained. Furthermore, the investigations made by the inventors reveal that the change in the threshold voltage becomes large in repeated driving. The large change in the threshold voltage brings about a problem that the transistor is deteriorated in reliability and may not be used for a prolonged period of time. The change in the threshold voltage after repeated driving is a problem that has not been known in the art.

Patent Document 3 describes the carbazole having two benzo-condensed rings, but Patent Document 3 does not describe an example of the application of the compound described therein to an organic transistor, and the use of the compounds described therein has failed to provide sufficient transistor characteristics (a low carrier mobility).

Under the circumstances, the inventors have made investigations for solving the problems in the related art. An object to be achieved by the invention is to provide an organic thin film transistor that has a high carrier mobility and a small change in the threshold voltage after repeated driving.

As a result of earnest investigations for solving the problems, the inventors have found that an organic thin film that is advantageous for carrier transport may be obtained by such a manner that in a compound having a dibenzocarbazole structure, the bulkiness of the substituent on the N atom of carbazole is reduced to such an extent that a sufficient overlap of electron orbitals is obtained with the adjacent molecule, and the particular substituent is introduced to the carbon atom constituting the ring of the dibenzocarbazole skeleton. It has been found that an organic thin film transistor having a high carrier mobility is obtained thereby.

Furthermore, the inventors have found that an organic thin film transistor that uses the dibenzocarbazole having the structure in a semiconductor active layer shows a small change in the threshold voltage after repeated driving, and thus have completed the invention.

The invention as a specific measure for solving the problems includes the following aspects.

(1) An organic thin film transistor containing a compound represented by the following formula (1) in a semiconductor active layer:

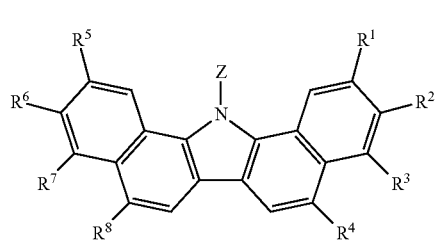

Formula (1)

wherein in the formula (1), Z represents a substituent that has a length of 3.7 Å or less from the N atom to the end of the substituent; and $R^1$ to $R^8$ each independently represent a hydrogen atom or a substituent, provided that at least one of $R^1$ to $R^8$ represents a substituent represented by the following formula (W):

-L-R     Formula (W)

wherein in the formula (W), L represents a divalent linking group represented by any one of the following formulae (L-1) to (L-12), or a divalent linking group containing 2 or more divalent linking groups each represented by any one of the following formulae (L-1) to (L-12) bonded to each other; and R represents a substituted or unsubstituted alkyl group having 2 or more carbon atoms, an oligooxyethylene group having a repeating number of an oxyethylene unit of 2 or more, or an oligosiloxane group having 2 or more silicon atoms:

(L-1)

(L-2)

(L-3)

(L-4)

(L-5)

(L-6)

(L-7)

(L-8)

(L-9)

(L-10)

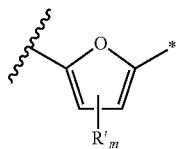
(L-11)

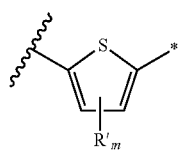
(L-12)

wherein in the formulae (L-1) to (L-12), the wavy line represents a position bonded to the dibenzocarbazole skeleton, and * represents a position bonded to R in the formula (W); in the formula (L-1), n represents an integer of 1 or more; in the formula (L-10), m represents 4; in the formulae (L-11) and (L-12), m represents 2; and in the formulae (L-1), (L-2), (L-10), (L-11) and (L-12), R' each independently represent a hydrogen atom or a substituent.

(2) In the organic thin film transistor according to the item (1), at least one of $R^2$, $R^3$, $R^6$ and $R^7$ preferably represents a substituent represented by the formula (W).

(3) In the organic thin film transistor according to the item (1), the compound represented by the formula (1) is preferably a compound represented by the following formula (2-1) or (2-2):

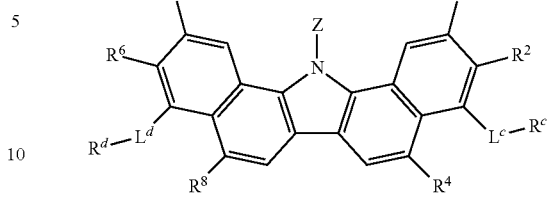
Formula (2-1)

wherein in the formula (2-1), $R^1$, $R^3$ to $R^5$, and $R^7$ to $R^8$ each independently represent a hydrogen atom or a substituent; $L^a$ and $L^b$ each independently represent a divalent linking group represented by any one of the following formulae (L-1) to (L-12), or a divalent linking group containing 2 or more divalent linking groups each represented by any one of the following formulae (L-1) to (L-12) bonded to each other; and $R^a$ and $R^b$ each independently represent a substituted or unsubstituted alkyl group having 2 or more carbon atoms, an oligooxyethylene group having a repeating number of an oxyethylene unit of 2 or more, or an oligosiloxane group having 2 or more silicon atoms,

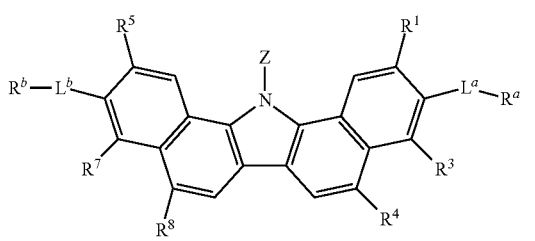
Formula (2-2)

wherein in the formula (2-2), $R^1$, $R^2$, $R^4$ to $R^6$, and $R^8$ each independently represent a hydrogen atom or a substituent; $L^c$ and $L^d$ each independently represent a divalent linking group represented by any one of the following formulae (L-1) to (L-12), or a divalent linking group containing 2 or more divalent linking groups each represented by any one of the following formulae (L-1) to (L-12) bonded to each other; and $R^c$ and $R^d$ each independently represent a substituted or unsubstituted alkyl group having 2 or more carbon atoms, an oligooxyethylene group having a repeating number of an oxyethylene unit of 2 or more, or an oligosiloxane group having 2 or more silicon atoms:

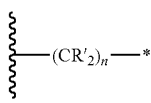
(L-1)

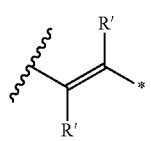
(L-2)

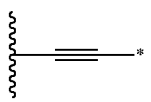
(L-3)

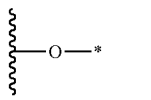
(L-4)

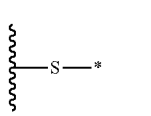
(L-5)

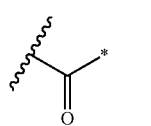
(L-6)

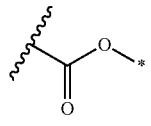
(L-7)

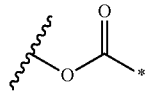
(L-8)

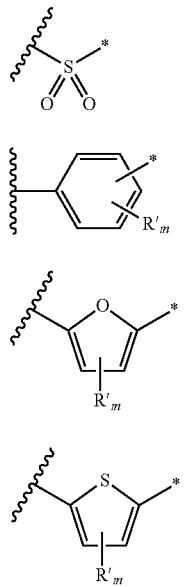

wherein in the formulae (L-1) to (L-12) in the formulae (2-1) and (2-2), the wavy line represents a position bonded to the dibenzocarbazole skeleton, and * each independently represents a position bonded to any one of $R^a$, $R^b$, $R^c$ and $R^d$ adjacent to the formulae (L-1) to (L-12); in the formula (L-1), n represents an integer of 1 or more; in the formula (L-10), m represents 4; in the formulae (L-11) and (L-12), m represents 2; and in the formulae (L-1), (L-2), (L-10), (L-11) and (L-12), R' each independently represent a hydrogen atom or a substituent.

(4) In the organic thin film transistor according to the item (3), in the formula (2-1) or (2-2), Z preferably represents a hydrogen atom, a substituted or unsubstituted alkyl group having 2 or less carbon atoms, a substituted or unsubstituted alkynyl group having 2 or less carbon atoms, a substituted or unsubstituted alkenyl group having 2 or less carbon atoms, or a substituted or unsubstituted acyl group having 2 or less carbon atoms.

(5) In the organic thin film transistor according to the item (3) or (4), in the formula (2-1) or (2-2), all of $L^a$, $L^b$, $L^c$ and $L^d$ each preferably represent a divalent linking group represented by any one of the formulae (L-1) to (L-3), (L-10), (L-11) or (L-12), or a divalent linking group containing 2 or more of the divalent linking groups bonded to each other.

(6) In the organic thin film transistor according to the item (3) or (4), in the formula (2-1) or (2-2), all of $L^a$, $L^b$, $L^c$ and $L^d$ each preferably represent a divalent linking group represented by the formula (L-1) or (L-10).

(7) In the organic thin film transistor according to any one of the items (3) to (6), in the formula (2-1) or (2-2), all $R^a$, $R^b$, $R^c$ and $R^d$ each preferably represent an alkyl group having 2 or more carbon atoms.

(8) In the organic thin film transistor according to any one of the items (3) to (6), in the formula (2-1) or (2-2), all $R^a$, $R^b$, $R^c$ and $R^d$ each preferably represent a linear alkyl group having from 3 to 12 carbon atoms.

(9) A compound represented by the following formula (1):

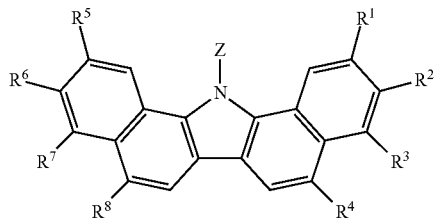

Formula (1)

wherein in the formula (1), Z represents a substituent that has a length of 3.7 Å or less from the N atom to the end of the substituent; and $R^1$ to $R^8$ each independently represent a hydrogen atom or a substituent, provided that at least one of $R^1$ to $R^8$ represents a substituent represented by the following formula (W):

-L-R    Formula (W)

wherein in the formula (W), L represents a divalent linking group represented by any one of the following formulae (L-1) to (L-12), or a divalent linking group containing 2 or more divalent linking groups each represented by any one of the following formulae (L-1) to (L-12) bonded to each other; and R represents a substituted or unsubstituted alkyl group having 2 or more carbon atoms, an oligooxyethylene group having a repeating number of an oxyethylene unit of 2 or more, or an oligosiloxane group having 2 or more silicon atoms:

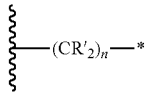

(L-1)

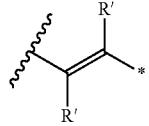

(L-2)

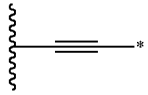

(L-3)

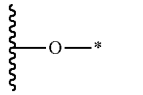

(L-4)

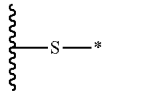

(L-5)

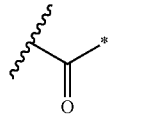

(L-6)

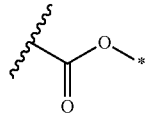

(L-7)

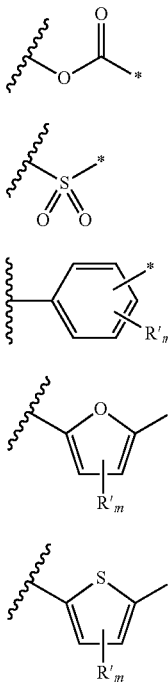

(L-8)

(L-9)

(L-10)

(L-11)

(L-12)

wherein in the formulae (L-1) to (L-12), the wavy line represents a position bonded to the dibenzocarbazole skeleton, and * represents a position bonded to R in the formula (W); in the formula (L-1), n represents an integer of 1 or more; in the formula (L-10), m represents 4; in the formulae (L-11) and (L-12), m represents 2; and in the formulae (L-1), (L-2), (L-10), (L-11) and (L-12), R' each independently represent a hydrogen atom or a substituent.

(10) In the compound according to the item (9), at least one of $R^2$, $R^3$, $R^6$ and $R^7$ preferably represents a substituent represented by the formula (W).

(11) In the compound according to the item (9), the compound represented by the formula (1) is preferably a compound represented by the following formula (2-1) or (2-2):

Formula (2-1)

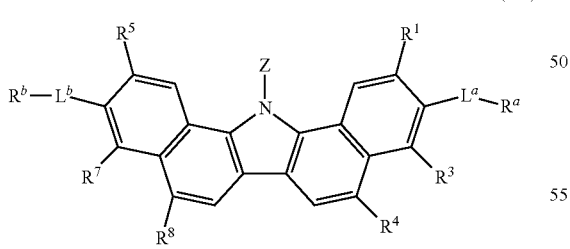

wherein in the formula (2-1), $R^1$, $R^3$ to $R^5$, and $R^7$ to $R^8$ each independently represent a hydrogen atom or a substituent; $L^a$ and $L^b$ each independently represent a divalent linking group represented by any one of the following formulae (L-1) to (L-12), or a divalent linking group containing 2 or more divalent linking groups each represented by any one of the following formulae (L-1) to (L-12) bonded to each other; and $R^a$ and $R^b$ each independently represent a substituted or unsubstituted alkyl group having 2 or more carbon atoms, an oligooxyethylene group having a repeating number of an oxyethylene unit of 2 or more, or an oligosiloxane group having 2 or more silicon atoms, Formula (2-2)

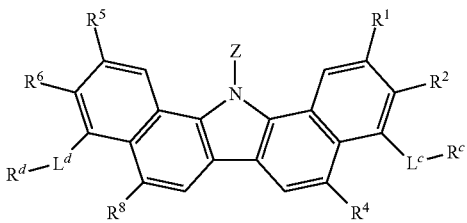

wherein in the formula (2-2), $R^1$, $R^2$, $R^4$ to $R^6$, and $R^8$ each independently represent a hydrogen atom or a substituent; $L^c$ and $L^d$ each independently represent a divalent linking group represented by any one of the following formulae (L-1) to (L-12), or a divalent linking group containing 2 or more divalent linking groups each represented by any one of the following formulae (L-1) to (L-12) bonded to each other; and $R^c$ and $R^d$ each independently represent a substituted or unsubstituted alkyl group having 2 or more carbon atoms, an oligooxyethylene group having a repeating number of an oxyethylene unit of 2 or more, or an oligosiloxane group having 2 or more silicon atoms:

(L-1)

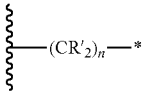

(L-2)

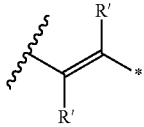

(L-3)

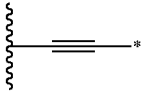

(L-4)

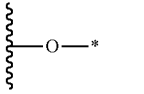

(L-5)

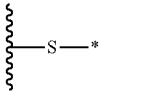

(L-6)

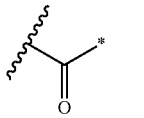

(L-7)

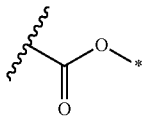

-continued

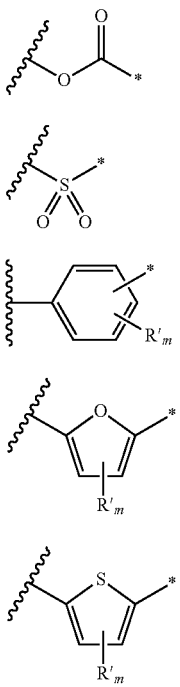

wherein in the formulae (L-1) to (L-12) in the formulae (2-1) and (2-2), the wavy line represents a position bonded to the dibenzocarbazole skeleton, and * each independently represents a position bonded to any one of $R^a$, $R^b$, $R^c$ and $R^d$ adjacent to the formulae (L-1) to (L-12); in the formula (L-1), n represents an integer of 1 or more; in the formula (L-10), m represents 4; in the formulae (L-11) and (L-12), m represents 2; and in the formulae (L-1), (L-2), (L-10), (L-11) and (L-12), R' each independently represent a hydrogen atom or a substituent.

(12) In the compound according to the item (11), in the formula (2-1) or (2-2), Z preferably represents a hydrogen atom, a substituted or unsubstituted alkyl group having 2 or less carbon atoms, a substituted or unsubstituted alkynyl group having 2 or less carbon atoms, a substituted or unsubstituted alkenyl group having 2 or less carbon atoms, or a substituted or unsubstituted acyl group having 2 or less carbon atoms.

(13) In the compound according to the item (11) or (12), in the formula (2-1) or (2-2), all of $L^a$, $L^b$, $L^c$ and $L^d$ each preferably represent a divalent linking group represented by any one of the formulae (L-1) to (L-3), (L-10), (L-11) or (L-12), or a divalent linking group containing 2 or more of the divalent linking groups bonded to each other.

(14) In the compound according to the item (11) or (12), in the formula (2-1) or (2-2), all of $L^a$, $L^b$, $L^c$ and $L^d$ each preferably represent a divalent linking group represented by the formula (L-1) or (L-10).

(15) In the compound according to any one of the items (11) to (14), in the formula (2-1) or (2-2), all $R^a$, $R^b$, $R^c$ and $R^d$ each preferably represent an alkyl group having 2 or more carbon atoms.

(16) In the compound according to any one of the items (11) to (14), in the formula (2-1) or (2-2), all $R^a$, $R^b$, $R^c$ and $R^d$ each preferably represent a linear alkyl group having from 3 to 12 carbon atoms.

(17) An organic semiconductor material for a non-light emitting organic semiconductor device, containing the compound represented by the formula (1) according to any one of the items (9) to (16).

(18) A material for an organic thin film transistor, containing the compound represented by the formula (1) according to any one of the items (9) to (16).

(19) A coating solution for a non-light emitting organic semiconductor device, containing the compound represented by the formula (1) according to any one of the items (9) to (16).

(20) A coating solution for a non-light emitting organic semiconductor device, containing the compound represented by the formula (1) according to any one of the items (9) to (16), and a polymer binder.

(21) An organic semiconductor thin film for a non-light emitting organic semiconductor device, containing the compound represented by the formula (1) according to anyone of the items (9) to (16).

(22) An organic semiconductor thin film for a non-light emitting organic semiconductor device, containing the compound represented by the formula (1) according to anyone of the items (9) to (16), and a polymer binder.

(23) The organic semiconductor thin film for a non-light emitting organic semiconductor device according to the item (21) or (22) is preferably produced by a solution coating method.

According to the invention, an organic thin film transistor may be provided that has a high carrier mobility and a small change in the threshold voltage after repeated driving.

BRIEF DESCRIPTION OF DRAWINGS

In FIGS. 1 and 2, 11 is substrate, 12 is electrode, 13 is insulating layer, 14 is semiconductor active layer (organic material layer or organic semiconductor layer), 15a, 15b are each electrode, 31 is substrate, 32 is electrode, 33 is insulating layer, 34a, 34b is electrode, and 35 is semiconductor active layer (organic material layer or organic semiconductor layer)

DESCRIPTION OF EMBODIMENTS

Figure 1:
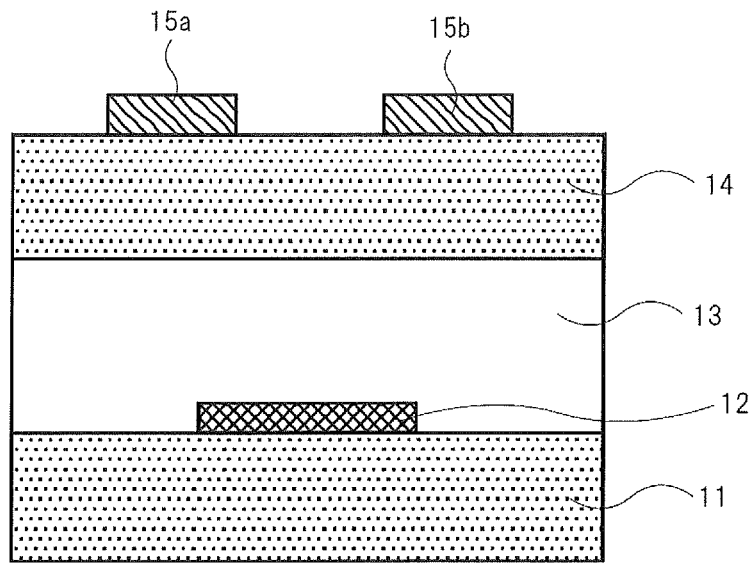
FIG. 1 is a schematic illustration showing a cross sectional structure of one example of the organic thin film transistor of the invention.

The invention will be described in detail below. The description for the constitutional components shown below may be made with reference to representative embodiments and specific examples, but the invention is not limited to the embodiments and the examples. In the description, a numerical range expressed with reference to an upper limit and/or a lower limit means a range that includes the upper limit and/or the lower limit.

In the invention, the hydrogen atom that is referred without any particular discrimination in the description of the formulae herein includes isotopes thereof (such as a deuterium atom). The atoms constituting the substituents also include isotopes thereof.

Organic Thin Film Transistor

The organic thin film transistor of the invention contains a compound represented by the following formula (1) in a semiconductor active layer:

Formula (1)

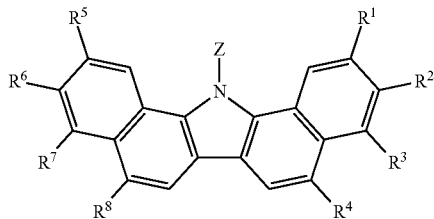

wherein in the formula (1), Z represents a substituent that has a length of 3.7 Å or less from the N atom to the end of the substituent; and $R^1$ to $R^8$ each independently represent a hydrogen atom or a substituent, provided that at least one of $R^1$ to $R^8$ represents a substituent represented by the following formula (W):

-L-R    Formula (W)

wherein in the formula (W), L represents a divalent linking group represented by any one of the following formulae (L-1) to (L-12), or a divalent linking group containing 2 or more divalent linking groups each represented by any one of the following formulae (L-1) to (L-12) bonded to each other; and R represents a substituted or unsubstituted alkyl group having 2 or more carbon atoms, an oligooxyethylene group having a repeating number of an oxyethylene unit of 2 or more, or an oligosiloxane group having 2 or more silicon atoms:

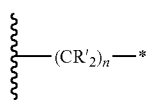   (L-1)

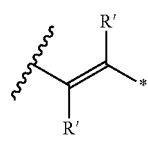   (L-2)

(L-3)

(L-4)

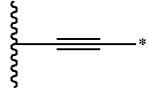   (L-5)

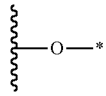   (L-6)

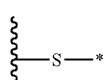   (L-7)

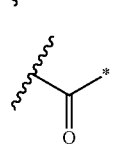   (L-8)

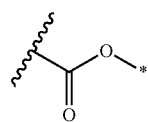   (L-9)

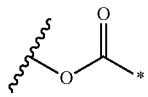   (L-10)

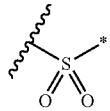

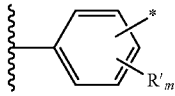   (L-11)

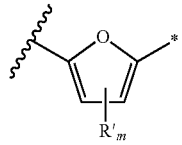   (L-12)

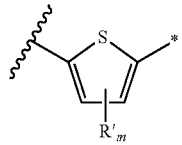

wherein in the formulae (L-1) to (L-12), the wavy line represents a position bonded to the dibenzocarbazole skeleton, and * represents a position bonded to R in the formula (W); in the formula (L-1), n represents an integer of 1 or more; in the formula (L-10), m represents 4; in the formulae (L-11) and (L-12), m represents 2; and in the formulae (L-1), (L-2), (L-10), (L-11) and (L-12), R' each independently represent a hydrogen atom or a substituent.

According to the constitution, the organic thin film transistor of the invention has a high carrier mobility and a small change in the threshold voltage after repeated driving.

The compound represented by the formula (1) has a substituent represented by the formula (W) as at least one of $R^1$ to $R^8$, and thus is preferred from the standpoint of the applicability of the material to a solution process and the molecular orientation in the film. According to the structure, the production efficiency of the organic thin film that is applicable to an organic thin film transistor may be increased to suppress the production cost. Furthermore, the carrier transport property including the carrier mobility, and the chemical stability and the physical stability of the thin film may also be enhanced. Accordingly, an organic thin film transistor having a high carrier mobility may be obtained.

For reducing the change in the threshold voltage after repeated driving, there are such requirements as chemical stability of the organic semiconductor material (particularly, air oxidation resistance and redox stability), thermal stability in the form of a thin film, a large film density capable of preventing air and water from invading, a film quality with less defects capable of preventing charges from being accumulated, and the like. It is considered that the compound represented by the formula (1) satisfies these requirements and thus has a small change in the threshold voltage after repeated driving. Accordingly, the organic thin film transistor of the invention having a less change in the threshold voltage after repeated driving has a semiconductor active layer that has a high chemical stability, a high film density, and the like, and thus effectively functions as a transistor for a prolonged period of time.

JP-A-2012-513459 does not describe a compound that has the same skeleton as the compound represented by the formula (1), but describes a structural isomer of the compound represented by the formula (1). However, the structural isomer has a low carrier mobility. WO 2010/114264 describes a compound that has the same skeleton as the compound represented by the formula (1), but the substituent on the N atom of carbazole has high bulkiness, and the compound has a low carrier mobility due to an insufficient overlap of electron orbitals with the adjacent molecule. In the invention, on the other hand, the advantageous effects of the invention may be obtained by using, as an organic semiconductor material, the compound that has a skeleton represented by the formula (1), has a bulkiness of the substituent on the N atom of carbazole that is reduced to such an extent that provides a sufficient overlap of electron orbitals with the adjacent molecule, and has the particular substituent introduced to the carbon atom constituting the ring of the dibenzocarbazole skeleton.

Preferred embodiments of the compound of the invention, the organic thin film transistor of the invention, and the like will be described below.

Compound Represented by Formula (1)

The compound of the invention is represented by the following formula (1). The compound of the invention is contained in a semiconductor active layer described later in the organic thin film transistor of the invention. Thus, the compound of the invention may be used as a material for an organic thin film transistor.

Formula (1)

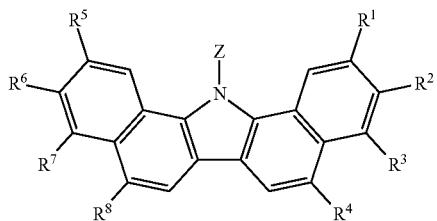

wherein in the formula (1), Z represents a substituent that has a length of 3.7 Å or less from the N atom to the end of the substituent; and $R^1$ to $R^8$ each independently represent a hydrogen atom or a substituent, provided that at least one of $R^1$ to $R^8$ represents a substituent represented by the following formula (W):

-L-R    Formula (W)

wherein in the formula (W), L represents a divalent linking group represented by any one of the following formulae (L-1) to (L-12), or a divalent linking group containing 2 or more divalent linking groups each represented by any one of the following formulae (L-1) to (L-12) bonded to each other; and R represents a substituted or unsubstituted alkyl group having 2 or more carbon atoms, an oligooxyethylene group having a repeating number of an oxyethylene unit of 2 or more, or an oligosiloxane group having 2 or more silicon atoms:

(L-1)

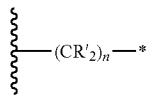

(L-2)

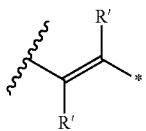

(L-3)

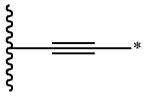

(L-4)

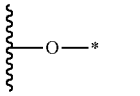

(L-5)

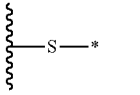

(L-6)

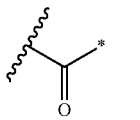

(L-7)

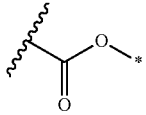

(L-8)

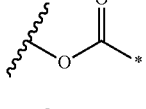

(L-9)

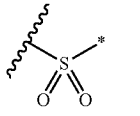

(L-10)

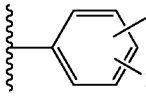

(L-11)

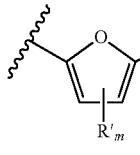

(L-12)

wherein in the formulae (L-1) to (L-12), the wavy line represents a position bonded to the dibenzocarbazole skeleton, and * represents a position bonded to R in the formula (W); in the formula (L-1), n represents an integer of 1 or more; in the formula (L-10), m represents 4; in the formulae (L-11) and (L-12), m represents 2; and in the formulae (L-1), (L-2), (L-10), (L-11) and (L-12), R' each independently represent a hydrogen atom or a substituent.

In the formula (1), Z represents a substituent that has a length of 3.7 Å or less from the N atom to the end of the substituent. The molecular length of the substituent Z herein means the length of from the N atom in the N—Z bond in carbazole of the dibenzocarbazole structure to the end of the substituent represented by Z. The structure optimization calculation may be performed by the density functional approach (Gaussian 03 (Gaussian, Inc., U.S.), base function: 6-31G*, exchange correlation function: B3LYP/LANL2DZ). In the formula (1), Z preferably represents a substituent that has a length of from 1.0 to 3.7 Å from the N atom to the end of the substituent, and more preferably a substituent that has a length of from 1.0 to 2.1 Å. The molecular lengths of representative substituents are 4.6 Å for a propyl group, 4.6 Å for a pyrrol group, 4.5 Å for a propynyl group, 4.6 Å for propenyl group, 4.5 Å for an ethoxy group, 3.7 Å for a methylthio group, 3.4 Å for an ethenyl group, 3.5 Å for an ethyl group, 3.6 Å for an ethynyl group, 3.3 Å for a methoxy group, 2.1 Å for a methyl group, and 1.0 Å for a hydrogen atom.

In the formula (1), Z preferably represents a hydrogen atom, a substituted or unsubstituted alkyl group having 2 or less carbon atoms, a substituted or unsubstituted alkynyl group having 2 or less carbon atoms, a substituted or unsubstituted alkenyl group having 2 or less carbon atoms, or a substituted or unsubstituted acyl group having 2 or less carbon atoms, more preferably a hydrogen atom or a substituted or unsubstituted alkyl group having 2 or less carbon atoms, and particularly preferably a hydrogen atom.

In the case where Z represents a substituted alkyl group having 2 or less carbon atoms, examples of the substituent capable of being substituted on the alkyl group include a cyano group, a fluorine atom and a deuterium atom, and a cyano group is preferred. The number of carbon atoms of the substituted alkyl group represented by Z is preferably 1. The substituted or unsubstituted alkyl group having 2 or less carbon atoms represented by Z is preferably a methyl group, an ethyl group, or a methyl group substituted by a cyano group, more preferably a methyl group or a methyl group substituted by a cyano group, and particularly preferably a methyl group substituted by a cyano group.

In the case where Z represents a substituted alkynyl group having 2 or less carbon atoms, examples of the substituent capable of being substituted on the alkynyl group include a deuterium atom. Examples of the substituted or unsubstituted alkynyl group having 2 or less carbon atoms represented by Z include an ethynyl group and an acetylene group substituted by a deuterium atom, and an ethynyl group is preferred.

In the case where Z represents a substituted alkenyl group having 2 or less carbon atoms, examples of the substituent capable of being substituted on the alkenyl group include a deuterium atom. Examples of the substituted or unsubstituted alkenyl group having 2 or less carbon atoms represented by Z include an ethenyl group and an ethenyl group substituted by a deuterium atom, and an ethenyl group is preferred.

In the case where Z represents a substituted acyl group having 2 or less carbon atoms, examples of the substituent capable of being substituted on the acyl group include a fluorine atom. Examples of the substituted or unsubstituted acyl group having 2 or less carbon atoms represented by Z include a formyl group, an acetyl group, and an acetyl group substituted by a fluorine atom, and a formyl group is preferred.

In the formula (1), $R^1$ to $R^8$ each independently represent a hydrogen atom or a substituent, provided that at least one of $R^1$ to $R^8$ represents a substituent represented by the formula (W).

The compound represented by the formula (1) may contain a substituent other than the substituent represented by the formula (W).

Examples of the substituent that may be $R^1$ to $R^8$ in the formula (1) include a halogen atom, an alkyl group (including a cycloalkyl group, a bicycloalkyl group and a tricycloalkyl group), an alkenyl group (including a cycloalkenyl group and a bicycloalkenyl group), an alkynyl group, an aryl group, a heterocyclic group, a cyano group, a hydroxyl group, a nitro group, a carboxyl group, an alkoxy group, an aryloxy group, a silyloxy group, a heterocyclic oxy group, an acyloxy group, a carbamoyloxy group, an alkoxycarbonyloxy group, an aryloxycarbonyloxy group, an amino group (including an anilino group), an ammonia group, an acylamino group, an aminocarbonylamino group, an alkoxycarbonylamino group, an aryloxycarbonylamino group, a sulfamoylamino group, an alkyl- or arylsulfonylamino group, a mercapto group, an alkylthio group, an arylthio group, a heterocyclic thio group, a sulfamoyl group, a sulfo group, an alkyl- or arylsulfinyl group, an alkyl- or arylsulfonyl group, an acyl group, an aryloxycarbonyl group, an alkoxycarbonyl group, a carbamoyl group, an aryl- or heterocyclic azo group, an imide group, a phosphino group, a phosphinyl group, a phosphinyloxy group, a phosphinylamino group, a phosphono group, a silyl group, a hydrazino group, a ureido group, a boronic acid group ($—B(OH)_2$), a phosphato group ($—PO(OH)_2$), a sulphato group ($—OSO_3H$), and other known groups.

Among these, a halogen atom, an alkyl group and an aryl group are preferred, a fluorine atom, an alkyl group having from 1 to 3 carbon atoms and a phenyl group are more preferred, and an alkyl group having from 1 to 3 carbon atoms is particularly preferred.

In the compound represented by the formula (1), the number of the substituent other than the substituent represented by the formula (W) in $R^1$ to $R^8$ is preferably from 0 to 4, more preferably from 0 to 2, and particularly preferably 0.

The substituent represented by the formula (W) will be described.

In the formula (W), L represents a divalent linking group represented by any one of the following formulae (L-1) to (L-12), or a divalent linking group containing 2 or more divalent linking groups each represented by any one of the following formulae (L-1) to (L-12) bonded to each other.

(L-1)

(L-2)

(L-3)

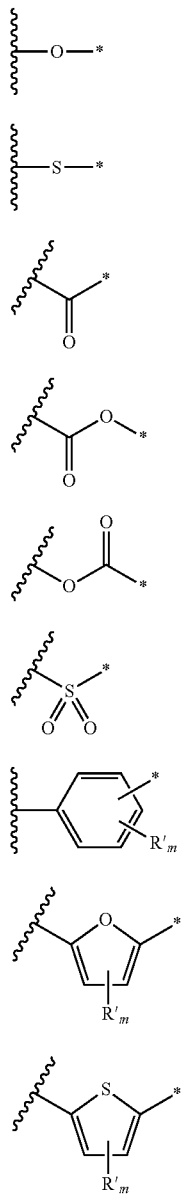

(L-4)
(L-5)
(L-6)
(L-7)
(L-8)
(L-9)
(L-10)
(L-11)
(L-12)

In the formulae (L-1) to (L-12), the wavy line represents a position bonded to the dibenzocarbazole skeleton, and * represents a position bonded to R in the formula (W); in the formula (L-1), n represents an integer of 1 or more; in the formula (L-10), m represents 4; in the formulae (L-11) and (L-12), m represents 2; and in the formulae (L-1), (L-2), (L-10), (L-11) and (L-12), R' each independently represent a hydrogen atom or a substituent.

In the case where L represents a divalent linking group containing divalent linking groups each represented by any one of the formulae (L-1) to (L-12) bonded to each other, the number of the divalent linking groups each represented by any one of the formulae (L-1) to (L-12) bonded to each other is preferably from 2 to 4, and more preferably 2 or 3.

Particularly in the formulae (L-10) to (L-12), it is also preferred that any one of the formulae (L-1) to (L-12) is further inserted between * and R to form L that represents a linking group containing divalent linking groups each represented by any one of the formulae (L-1) to (L-12) bonded to each other.

In the formula (L-1), n represents an integer of 1 or more, preferably an integer of from 1 to 10, more preferably an integer of from 1 to 6, and further preferably an integer of from 1 to 3.

Examples of the substituent R' in the formulae (L-1), (L-2), (L-10), (L-11) and (L-12) include the groups that are shown as examples of the other substituent that may be $R^1$ to $R^{10}$ in the formula (1).

In the formula (L-10), m represents 4; and in the formulae (L-11) and (L-12), m represents 2.

L preferably represents a divalent linking group represented by any one of the formulae (L-1) to (L-4), (L-6), (L-7), (L-9), (L-10), (L-11) and (L-12) or a divalent linking group containing 2 or more of the divalent linking groups bonded to each other, more preferably a divalent linking group represented by any one of the formulae (L-1) to (L-3), (L-10), (L-11) and (L-12) or a divalent linking group containing 2 or more of the divalent linking groups bonded to each other from the standpoint of the chemical stability and the carrier transport property, particularly preferably a divalent linking group represented by any one of the formulae (L-1), (L-3) and (L-10) or a divalent linking group containing 2 or more of the divalent linking groups bonded to each other, a divalent linking group represented by any one of the formulae (L-1) and (L-10), and further particularly preferably a divalent linking group represented by the formula (L-1).

In the formula (W), R represents a substituted or unsubstituted alkyl group having 2 or more carbon atoms, an oligooxyethylene group having a repeating number of an oxyethylene unit of 2 or more, or an oligosiloxane group having 2 or more silicon atoms.

In the case where R in the formula (W) represents a substituted or unsubstituted alkyl group having 2 or more carbon atoms, the number of carbon atoms thereof is preferably from 2 to 18, more preferably from 3 to 12 from the standpoint of the chemical stability and the carrier transport property, and further preferably from 4 to 10.

In the compound represented by the formula (1), in the case where the group represented by the formula (W) contains an alkyl group, a high carrier mobility may be obtained when the alkyl group represented by R has a carbon number that is the lower limit of the aforementioned range or more. In the case where L contains the formula (L-1) adjacent to R, a high carrier mobility may be obtained when the alkyl group formed by bonding the alkylene group represented by the formula (L-1) and the alkyl group represented by R has a carbon number that is the lower limit of the aforementioned range or more.

The alkyl group that may be R may be any one of linear, branched and cyclic, and is preferably a linear alkyl group from the standpoint of the enhancement of the carrier mobility, more preferably a linear alkyl group having from 3 to 12 carbon atoms, and particularly preferably a linear alkyl group having from 4 to 10 carbon atoms. In the case where R represents an alkyl group having a substituent, examples of the substituent include a halogen atom, and a fluorine atom is preferred. In the case where R represents an alkyl group having a fluorine atom, the alkyl group may be a perfluoroalkyl group, in which all the hydrogen atoms of the alkyl group are replaced by fluorine atoms.

In the case where R in the formula (W) represents an oligooxyethylene group having a repeating number of an oxyethylene group of 2 or more, the oxyethylene group represented by R herein means a group represented by —$(CH_2CH_2)_xOY$ (wherein the repeating number of an oxyethylene unit x is an integer of 2 or more, and Y as the terminal group represents a hydrogen atom or a substituent). In the case where Y as the terminal group of the oligooxyethylene group is a hydrogen atom, the group is a hydroxyl group. The repeating number of an oxyethylene unit x is preferably from 2 to 4, and more preferably from 2 to 3. The terminal hydroxyl group of the oligooxyethylene group is preferably blocked, i.e., Y preferably represents a substituent. In this case, the hydroxyl group is preferably blocked with an alkyl group having from 1 to 3 carbon atoms, i.e., Y preferably represents an alkyl group having from 1 to 3 carbon atoms, and Y more preferably represents a methyl group or an ethyl group, and particularly preferably a methyl group.

In the case where R in the formula (W) represents an oligosiloxane group having 2 or more silicon atoms, the repeating number of a siloxane unit is preferably from 2 to 4, and more preferably from 2 to 3. The Si atom is preferably bonded to a hydrogen atom or an alkyl group. In the case where the Si atom is bonded to an alkyl group, the number of carbon atoms of the alkyl group is preferably from 1 to 3, and for example, a methyl group or an ethyl group is preferably bonded thereto. The Si atom may be bonded to the same alkyl groups or may be bonded to different alkyl groups or a hydrogen atom. The siloxane units constituting the oligosiloxane group may be all the same as each other or different from each other, and are preferably all the same as each other.

In the compound represented by the formula (1), the number of the substituent that is represented by the formula (W) in $R^1$ to $R^8$ is preferably from 1 to 4, more preferably from 1 to 2, and particularly preferably 2.

In the formula (1) in the invention, at least one of $R^2$, $R^3$, $R^6$ and $R^7$ preferably represents a substituent represented by the formula (W). Furthermore, two positions of any one of $R^2$ and $R^3$ and any one of $R^6$ and $R^7$ are more preferably substituted.

It is considered that the reason why these positions are preferred as the substitution positions in the formula (1) is that the compound is excellent in chemical stability and is preferred from the standpoint of the HOMO level and the molecular packing in the film. In particular, when two positions of any one of $R^2$ and $R^3$ and any one of $R^6$ and $R^7$ each represent a substituent, a high carrier concentration may be obtained.

In the invention, the compound represented by the formula (1) is preferably a compound represented by the following formula (2-1) or (2-2).

Formula (2-1)

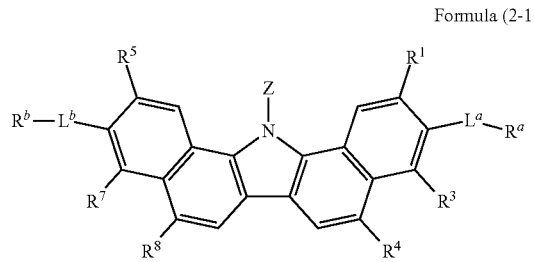

wherein in the formula (2-1), $R^1$, $R^3$ to $R^5$, and $R^7$ to $R^8$ each independently represent a hydrogen atom or a substituent; $L^a$ and $L^b$ each independently represent a divalent linking group represented by any one of the following formulae (L-1) to (L-12), or a divalent linking group containing 2 or more divalent linking groups each represented by any one of the following formulae (L-1) to (L-12) bonded to each other; and $R^a$ and $R^b$ each independently represent a substituted or unsubstituted alkyl group having 2 or more carbon atoms, an oligooxyethylene group having a repeating number of an oxyethylene unit of 2 or more, or an oligosiloxane group having 2 or more silicon atoms, Formula (2-2)

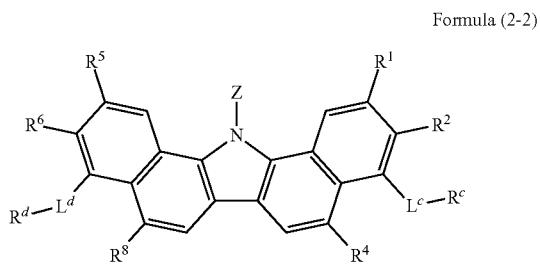

wherein in the formula (2-2), $R^1$, $R^2$, $R^4$ to $R^6$, and $R^8$ each independently represent a hydrogen atom or a substituent; $L^c$ and $L^d$ each independently represent a divalent linking group represented by any one of the following formulae (L-1) to (L-12), or a divalent linking group containing 2 or more divalent linking groups each represented by any one of the following formulae (L-1) to (L-12) bonded to each other; and $R^c$ and $R^d$ each independently represent a substituted or unsubstituted alkyl group having 2 or more carbon atoms, an oligooxyethylene group having a repeating number of an oxyethylene unit of 2 or more, or an oligosiloxane group having 2 or more silicon atoms,

(L-1)

(L-2)

(L-3)

(L-4)

(L-5)

(L-6)

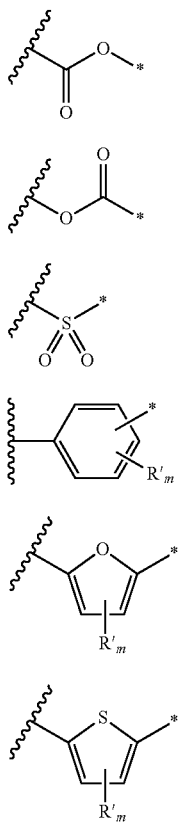

(L-7)

(L-8)

(L-9)

(L-10)

(L-11)

(L-12)

wherein in the formulae (L-1) to (L-12) in the formulae (2-1) and (2-2), the wavy line represents a position bonded to the dibenzocarbazole skeleton, and * each independently represents a position bonded to any one of $R^a$, $R^b$, $R^c$ and $R^d$ adjacent to the formulae (L-1) to (L-12); in the formula (L-1), n represents an integer of 1 or more; in the formula (L-10), m represents 4; in the formulae (L-11) and (L-12), m represents 2; and in the formulae (L-1), (L-2), (L-10), (L-11) and (L-12), R' each independently represent a hydrogen atom or a substituent.

In the formula (2-1), $R^1$, $R^3$ to $R^5$, and $R^7$ to $R^8$ each independently represent a hydrogen atom or a substituent. The preferred ranges of the substituents represented by $R^1$, $R^3$ to $R^5$, and $R^7$ to $R^8$ are the same as the preferred ranges of the substituents represented by $R^1$ to $R^8$ in the formula (1) other than the substituent represented by the formula (W).

In the formula (2-1), $L^a$ and $L^b$ each independently represent a divalent linking group represented by any one of the formulae (L-1) to (L-12), or a divalent linking group containing 2 or more divalent linking groups each represented by any one of the formulae (L-1) to (L-12) bonded to each other. The preferred ranges of $L^a$ and $L^b$ are the same as the preferred ranges of L in the formula (W). $L^a$ and $L^b$ are preferably the same as each other. In the formulae (L-1) to (L-12) in the formulae (2-1) and (2-2), * each independently represents a position bonded to any one of $R^a$, $R^b$, $R^c$ and $R^d$ adjacent to the formulae (L-1) to (L-12).

In the formula (2-1), $R^a$ and $R^b$ each independently represent a substituted or unsubstituted alkyl group having 2 or more carbon atoms, an oligooxyethylene group having a repeating number of an oxyethylene unit of 2 or more, or an oligosiloxane group having 2 or more silicon atoms. The preferred ranges of $R^a$ and $R^b$ are the same as the preferred ranges of R in the formula (W). $R^a$ and $R^b$ are preferably the same as each other.

In the formula (2-2), $R^1$, $R^2$, $R^4$ to $R^6$, and $R^8$ each independently represent a hydrogen atom or a substituent. The preferred ranges of the substituents represented by $R^1$, $R^2$, $R^4$ to $R^6$, and $R^8$ are the same as the preferred ranges of the substituents represented by $R^1$ to $R^8$ in the formula (1) other than the substituent represented by the formula (W).

In the formula (2-2), $L^a$ and $L^b$ each independently represent a divalent linking group represented by any one of the following formulae (L-1) to (L-12), or a divalent linking group containing 2 or more divalent linking groups each represented by any one of the following formulae (L-1) to (L-12) bonded to each other. The preferred ranges of $L^c$ and $L^d$ are the same as the preferred ranges of L in the formula (W). $L^c$ and $L^d$ are preferably the same as each other.

In the formula (2-2), $R^c$ and $R^d$ each independently represent a substituted or unsubstituted alkyl group having 2 or more carbon atoms, an oligooxyethylene group having a repeating number of an oxyethylene unit of 2 or more, or an oligosiloxane group having 2 or more silicon atoms. The preferred ranges of $R^c$ and $R^d$ are the same as the preferred ranges of R in the formula (W). $R^c$ and $R^d$ are preferably the same as each other.

In the formulae (2-1) and (2-2), all $R^a$, $R^b$, $R^c$ and $R^d$ each preferably represent an alkyl group having 2 or more carbon atoms, more preferably a linear alkyl group having from 3 to 12 carbon atoms, and particularly preferably a linear alkyl group having from 4 to 10 carbon atoms.

In the formulae (2-1) and (2-2), all $L^a$, $L^b$, $L^c$ and $L^d$ each preferably represent a group represented by any one of the formulae (L-1) to (L-4), (L-6), (L-7), (L-9), (L-10), (L-11) and (L-12), more preferably any one of the formulae (L-1) to (L-3), (L-10), (L-11) and (L-12) from the standpoint of the chemical stability and the carrier transport property, particularly preferably any one of the formulae (L-1), (L-3) and (L-10), further particularly preferably the formula (L-1) or (L-10), and still further particularly preferably the formula (L-1).

Specific examples of the compound represented by the formula (1) are shown below, but the compound represented by the formula (1) capable of being used in the invention is not construed as being limited to the specific examples.

Compound 1

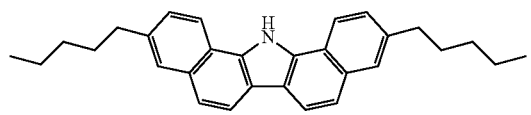

Compound 2

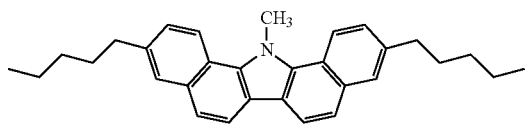

-continued
Compound 3
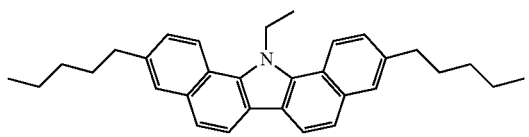
Compound 4
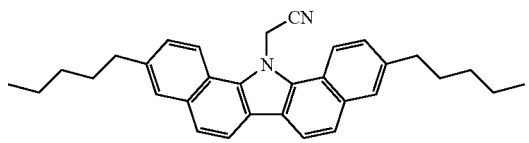
Compound 5
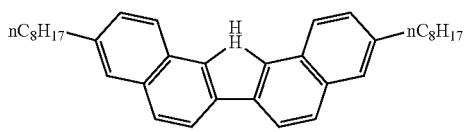
Compound 6
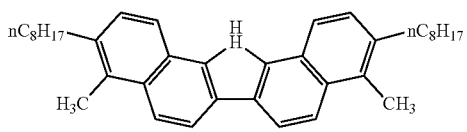
Compound 7
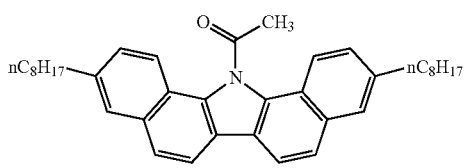
Compound 8
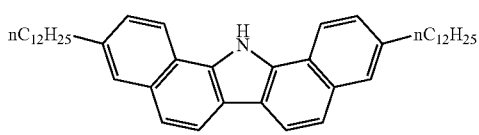
Compound 9
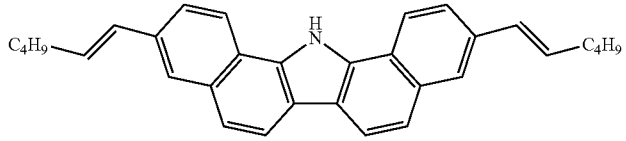
Compound 10
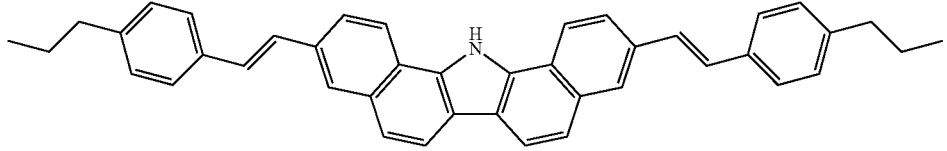
Compound 11
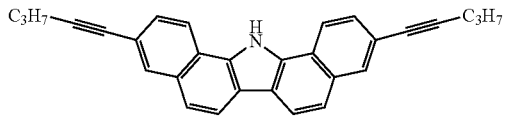
Compound 12
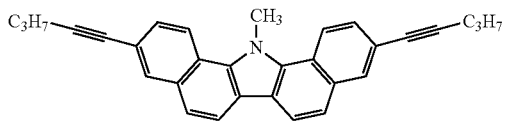
Compound 13
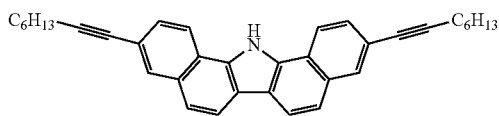
Compound 14
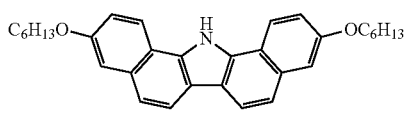
Compound 15
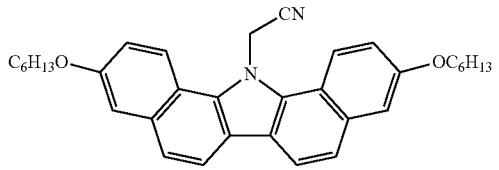
Compoud 16
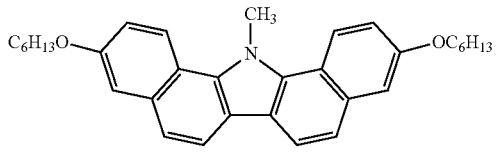
Compound 17
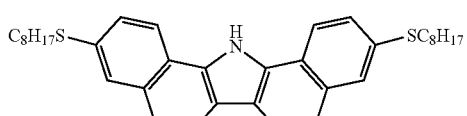
Compound 18
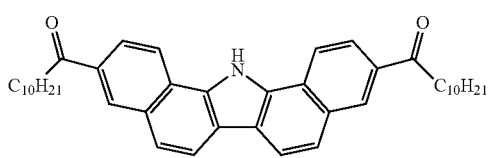

-continued
Compound 19
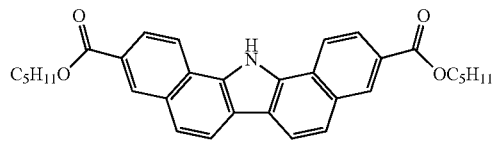
Compound 20
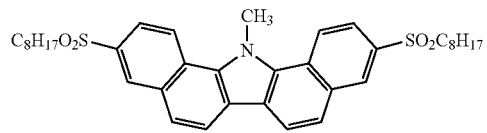
Compound 21
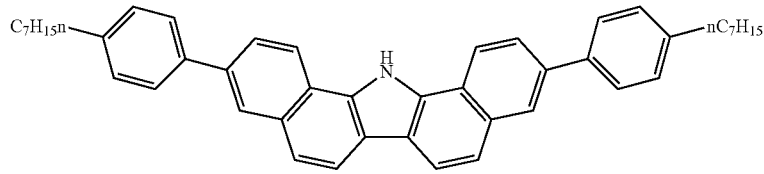
Compound 22
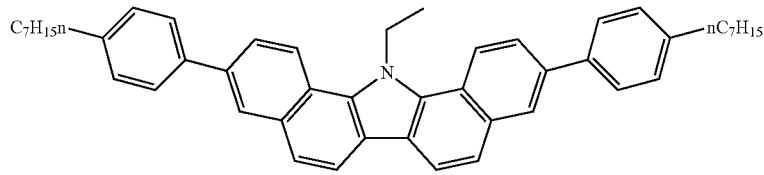
Ciompound 23
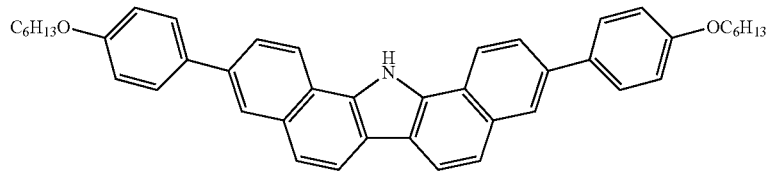
Compound 24
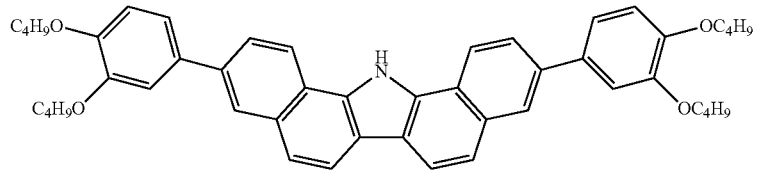
Compound 25
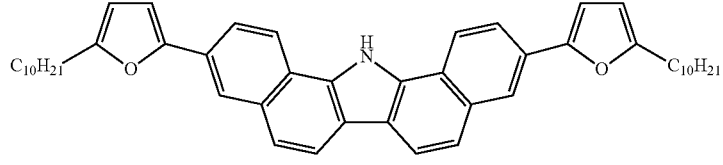
Compound 26
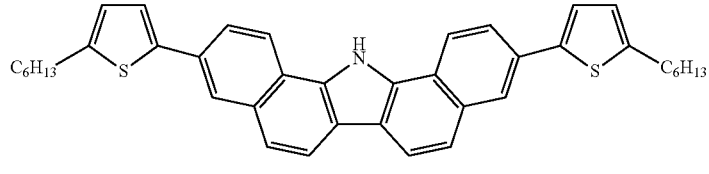
Compound 27
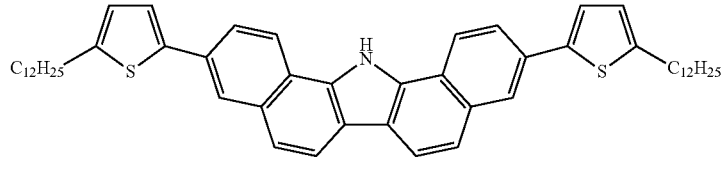
Compound 28
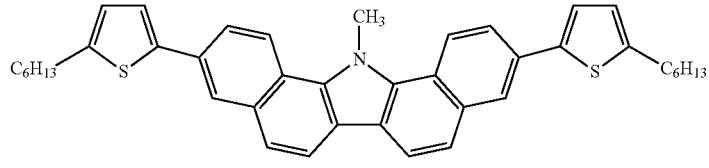

-continued
Compound 29
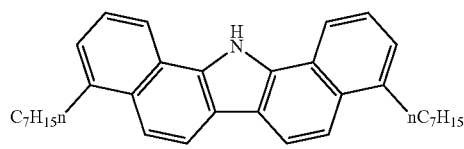
Compound 30
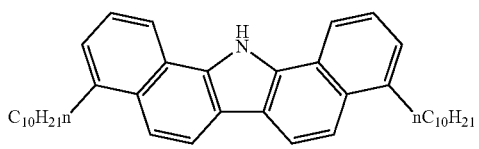
Compound 31
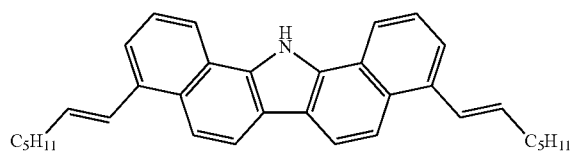
Compound 32
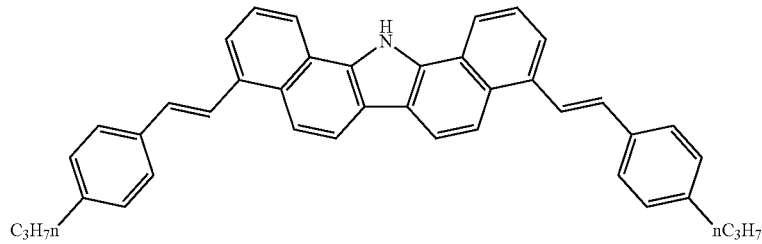
Compound 33
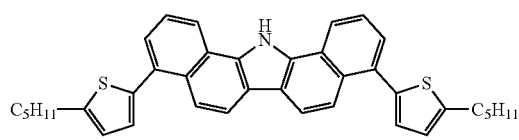
Compound 34
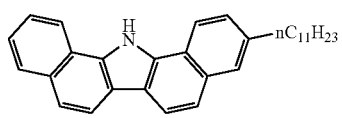
Compound 35
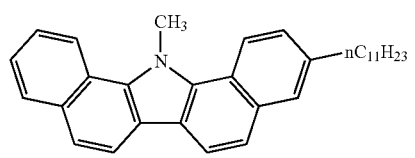
Compound 36
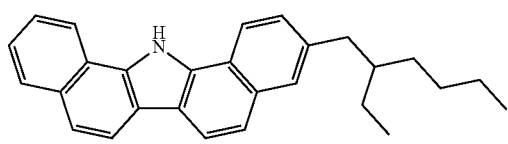
Compound 37
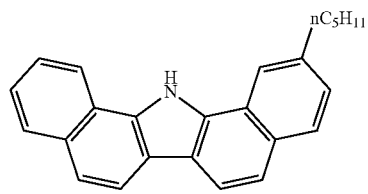
Compound 38
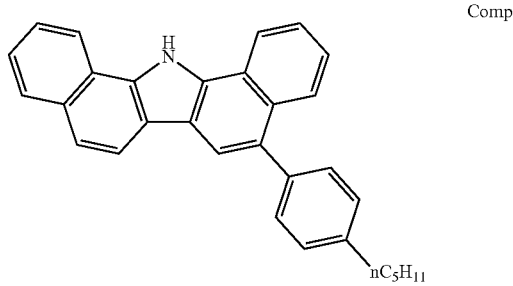
Compound 39
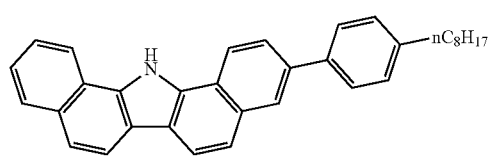
Compound 40
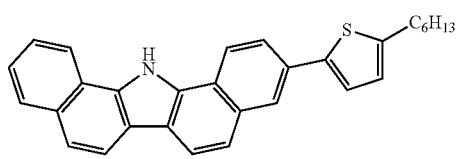
Compound 41
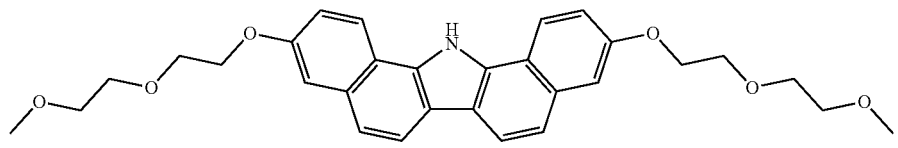

Compound 42

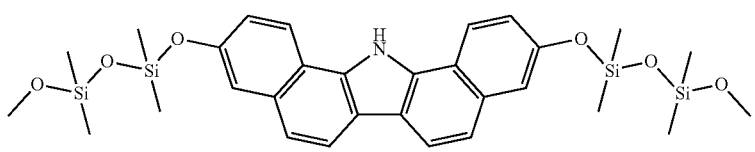

Compound 43

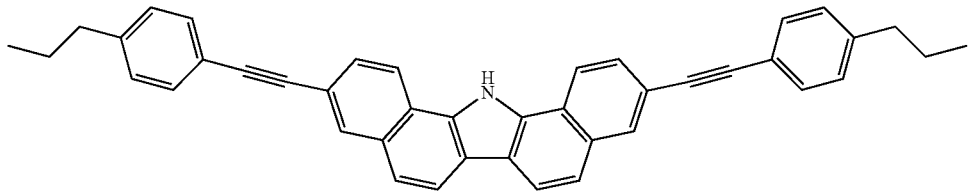

Compound 44

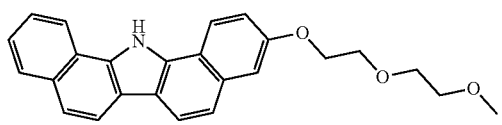

Compound 45

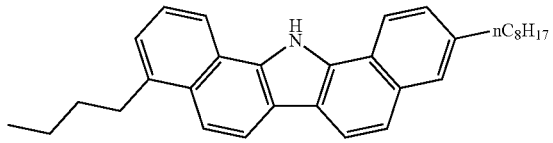

Compound 46

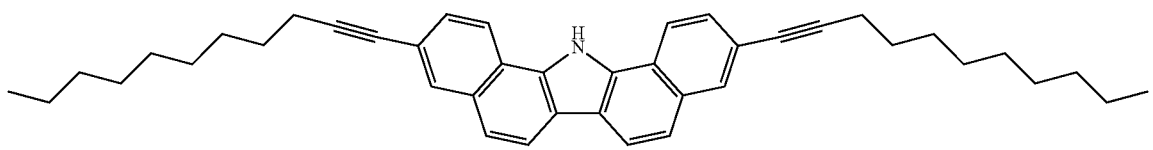

Compound 47

The compound represented by the formula (1) preferably has a molecular weight of 3,000 or less, more preferably 2,000 or less, further preferably 1,000 or less, and particularly preferably 850 or less. The molecular weight that is the upper limit or less is preferred since the compound has increased solubility in a solvent.

The molecular weight of the compound is preferably 400 or more, more preferably 450 or more, and further preferably 500 or more, from the standpoint of the stability of the film quality of the thin film.

The compound represented by the formula (1) may be synthesized by combining the method described in WO 2010/114264 and the known reactions.

In the reaction of forming the dibenzocarbazole ring of the compound of the invention, any reaction condition may be used. The reaction solvent used may be any solvent. An acid or a base is preferably used for promoting the ring-forming reaction, and particularly a base is preferably used. The optimum reaction condition may vary depending on the structure of the target dibenzocarbazole derivative, and may be determined with reference to the specific reaction shown in the aforementioned literature.

The synthesis intermediates having the various substituents may be synthesized by combining known reactions. The substituents may be introduced in any stage of the intermediates. The intermediates after synthesis is preferably purified by column chromatography, recrystallization or the like, and then purified by sublimation. The sublimation purification not only isolates organic impurities, but also effectively removes an inorganic salt, a residual solvent and the like.

Structure of Organic Thin Film Transistor

The organic thin film transistor of the invention has a semiconductor active layer containing the compound represented by the formula (1).

The organic thin film transistor of the invention may further contain other layers in addition to the semiconductor active layer.

The organic thin film transistor of the invention is preferably used as an organic field effect transistor (FET), and is more preferably used as an insulated gate FET, in which the gate and the channel are insulated from each other.

Preferred embodiments of the organic thin film transistor of the invention will be described below with reference to the drawings, but the invention is not limited to the embodiments.

Laminated Structure

The laminated structure of the organic field effect transistor is not particularly limited, and various known structures may be used.

One example of the structure of the organic thin film transistor of the invention is a bottom-gate top-contact structure having a substrate as the lowermost layer having disposed thereon an electrode, an insulating layer, a semiconductor active layer (organic semiconductor layer), and two electrodes, in this order. In this structure, the electrode on the upper surface of the substrate as the lowermost layer is provided on a part of the substrate, and the insulating layer is disposed to be in contact with the substrate in the portion other than the electrode. The two electrodes disposed on the upper surface of the semiconductor active layer are disposed to be separated from each other.

A structure of a bottom-gate top-contact device is shown in FIG. 1. FIG. 1 is a schematic illustration showing a cross sectional structure of one example of the organic thin film transistor of the invention. The organic thin film transistor shown in FIG. 1 has a substrate 11 disposed as the lowermost layer, an electrode 12 disposed on a part of the upper surface of the substrate 11, and an insulating layer 13 disposed to cover the electrode 12 and to be in contact with the substrate 11 in the portion other than the electrode 12. A semiconductor active layer 14 is provided on the upper surface of the insulating layer 13, and two electrodes 15a and 15b, which are separated from each other, are disposed on parts of the semiconductor active layer 14.

In the organic thin film transistor shown in FIG. 1, the electrode 12 is a gate, and the electrodes 15a and 15b each are a drain or a source. The organic thin film transistor shown in FIG. 1 is an insulated gate FET, in which the channel, which is an electric current path between the drain and the source, and the gate are insulated from each other.

Another example of the structure of the organic thin film transistor of the invention is a bottom-gate bottom-contact device.

Figure 2:
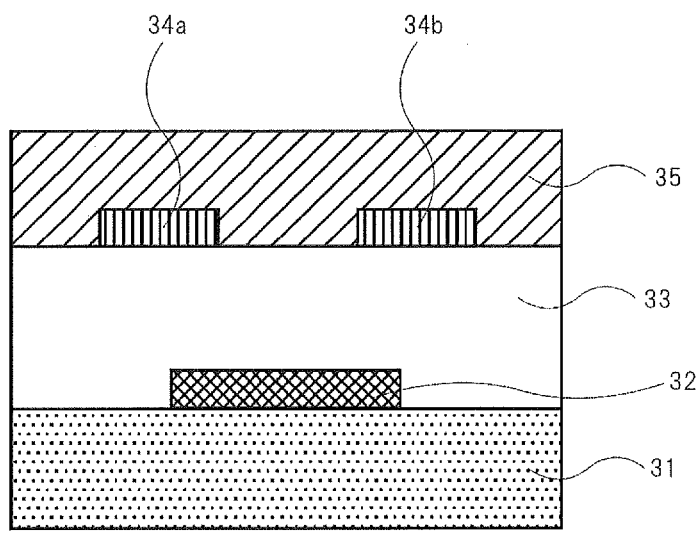
FIG. 2 is a schematic illustration showing a cross sectional structure of an organic thin film transistor that is produced as a substrate for measuring FET characteristics in the example of the invention.

A structure of a bottom-gate bottom-contact device is shown in FIG. 2. FIG. 2 is a schematic illustration showing a cross sectional structure of an organic thin film transistor that is produced as a substrate for measuring FET characteristics in the example of the invention. The organic thin film transistor shown in FIG. 2 has a substrate 31 disposed as the lowermost layer, an electrode 32 disposed on a part of the upper surface of the substrate 31, and an insulating layer 33 disposed to cover the electrode 32 and to be in contact with the substrate 31 in the portion other than the electrode 32. A semiconductor active layer 35 is provided on the upper surface of the insulating layer 33, and two electrodes 34a and 34b are disposed under the semiconductor active layer 35.

In the organic thin film transistor shown in FIG. 2, the electrode 32 is a gate, and the electrodes 34a and 34b each are a drain or a source. The organic thin film transistor shown in FIG. 2 is an insulated gate FET, in which the channel, which is an electric current path between the drain and the source, and the gate are insulated from each other.

Other preferred examples of the structure of the organic thin film transistor of the invention include a top-gate top-contact device and a top-gate bottom-contact device, in which an insulator and a gate electrode are disposed above a semiconductor active layer.
Thickness The organic thin film transistor of the invention preferably has a total thickness of the transistor, for example, of from 0.1 to 0.5 μm, in the case where a thinner transistor is demanded.
Sealing For shielding the organic thin film transistor device from the air and water to enhance the storage stability of the organic thin film transistor device, the entire organic thin film transistor device may be sealed with a metallic sealing canister, an inorganic material, such as glass and silicon nitride, a polymer material, such as parylene, a low molecular weight material, and the like.

Preferred embodiments of the layers of the organic thin film transistor of the invention will be described below, but the invention is not limited to the embodiments.
Substrate
Material The organic thin film transistor of the invention preferably contains a substrate.

The material for the substrate is not particularly limited, and known materials may be used. Examples of the material include a polyester film, such as polyethylene naphthoate (PEN) and polyethylene terephthalate (PET), a cycloolefin polymer film, a polycarbonate film, a triacetyl cellulose (TAC) film, a polyimide film, these polymer films having an ultrathin glass layer laminated thereon, ceramics, silicone, quartz, glass, and the like, and silicone is preferred.
Electrode
Material The organic thin film transistor of the invention preferably contains an electrode.

Examples of the material for the electrode include known electroconductive materials, for example, a metal material, such as Cr, Al, Ta, Mo, Nb, Cu, Ag, Au, Pt, Pd, In, Ni and Nd, an alloy material of the metal materials, a carbon material, and an electroconductive polymer, which may be used without particular limitation.
Thickness The thickness of the electrode is not particularly limited and is preferably from 10 to 50 nm.

The gate width (or the channel width) W and the gate length (or the channel length) L are not particularly limited, and the ratio W/L is preferably 10 or more, and more preferably 20 or more.
Insulating Layer
Material The material for the insulating layer is not particularly limited as far as the necessary insulating effect is obtained, and examples thereof include silicon dioxide, silicon nitride, a fluorine polymer insulating material, such as PTFE and CYTOP, a polyester insulating material, a polycarbonate insulating material, an acrylic polymer insulating material, an epoxy resin insulating material, a polyimide insulating material, a polyvinylphenol resin insulating material, and a poly-p-xylylene resin insulating material.

The upper surface of the insulating layer may be surface-treated, and preferred examples thereof used include an insulating layer formed of silicon dioxide, the surface of which is surface-treated by coating hexamethyldisilazane (HMDS) or octadecyltrichlorosilane (OTS) thereon.
Thickness The thickness of the insulating layer is not particularly limited, and in the case where a thin insulating layer is demanded, the thickness thereof is preferably from 10 to 400 nm, more preferably from 20 to 200 nm, and particularly preferably from 50 to 200 nm.
Semiconductor Active Layer
Material The organic thin film transistor of the invention contains the compound represented by the formula (1), i.e., the compound of the invention, in the semiconductor active layer.

The semiconductor active layer may be a layer that is formed of the compound of the invention, or a layer containing a polymer binder described later in addition to the compound of the invention. The semiconductor active layer may contain a residual solvent used on forming the film.

The content of the polymer binder in the semiconductor active layer is not particularly limited, and the polymer binder is preferably used in a range of from 0 to 95% by mass, more preferably used in a range of from 10 to 90% by mass, further preferably used in a range of from 20 to 80% by mass, and particularly preferably used in a range of from 30 to 70% by mass.

Thickness

The thickness of the semiconductor active layer is not particularly limited, and in the case where a thin semiconductor active layer is demanded, the thickness thereof is preferably from 10 to 400 nm, more preferably from 10 to 200 nm, and particularly preferably from 10 to 100 nm.

Organic Semiconductor Material for Non-Light Emitting Organic Semiconductor Device The invention also relates to an organic semiconductor material for a non-light emitting organic semiconductor device containing the compound represented by the formula (1), i.e., the compound of the invention.

Non-Light Emitting Organic Semiconductor Device

The non-light emitting organic semiconductor device referred herein means a device that is not intended to emit light. The non-light emitting organic semiconductor device is preferably a non-light emitting organic semiconductor device that uses an electronic element having a layer structure of thin films. The non-light emitting organic semiconductor device encompasses an organic thin film transistor, an organic photoelectric conversion device (such as a solid state imaging device for a photosensor, and a solar cell for energy conversion), a gas sensor, an organic rectifying device, an organic inverter, an information recording device, and the like. The organic photoelectric conversion device may be used for both a photosensor (i.e., a solid state imaging device) and energy conversion (i.e., a solar cell). Preferred examples of the device include an organic photoelectric conversion device and an organic thin film transistor, and more preferred examples thereof include an organic thin film transistor. Accordingly, the organic semiconductor device for a non-light emitting organic semiconductor device of the invention is preferably a material for an organic thin film transistor as described above.

Organic Semiconductor Material

The organic semiconductor material referred herein means an organic material that shows characteristics of a semiconductor. The organic semiconductor material includes a p-type (hole transporting) organic semiconductor, which shows conductivity with holes as a carrier, and an n-type (electron transporting) organic semiconductor, which shows conductivity with electrons as a carrier, as similar to a semiconductor material formed of an inorganic material.

The compound of the invention may be used as any of a p-type organic semiconductor material and an n-type organic semiconductor material, and is preferably used as a p-type organic semiconductor material. The flowability of a carrier in an organic semiconductor is shown by a carrier mobility $\mu$. The carrier mobility $\mu$ is preferably as large as possible, and is preferably $1 \times 10^{-3}$ cm$^2$/Vs or more, more preferably $5 \times 10^{-3}$ cm$^2$/Vs or more, particularly preferably $1 \times 10^{-2}$ cm$^2$/Vs or more, further particularly preferably $1 \times 10^{-1}$ cm$^2$/Vs or more, and still further particularly preferably 1 cm$^2$/Vs or more. The carrier mobility $\mu$ may be obtained from the characteristics of a field effect transistor (FET) device produced or by a time-of-flight (TOF) measurement method.

Organic Semiconductor Thin Film for Non-Light Emitting Organic Semiconductor Device Material The invention also relates to an organic semiconductor thin film for a non-light emitting organic semiconductor device containing the compound represented by the formula (1), i.e., the compound of the invention.

The organic semiconductor thin film for a non-light emitting organic semiconductor device of the invention contains the compound represented by the formula (1), i.e., the compound of the invention, and an embodiment thereof that contains no polymer binder is also preferred.

The organic semiconductor thin film for a non-light emitting organic semiconductor device of the invention may contain the compound represented by the formula (1), i.e., the compound of the invention, and a polymer binder.

Examples of the polymer binder include an insulating polymer, such as polystyrene, polycarbonate, polyarylate, polyester, polyamide, polyimide, polyurethane, polysiloxane, polysulfone, polymethyl methacrylate, polymethyl acrylate, cellulose, polyethylene and polypropylene, copolymers thereof, a photoconductive polymer, such as polyvinylcarbazole and polysilane, and an electroconductive polymer and a semiconductor polymer, such as polythiophene, polypyrrole, polyaniline and poly-p-phenylenevinylene.

The polymer binder may be used solely or as a combination of plural kinds thereof.

The organic semiconductor material and the polymer binder may be uniformly mixed, or a part or the whole thereof may be phase-separated, and from the standpoint of the charge mobility, such a structure that the organic semiconductor and the binder are phase-separated in the thickness direction in the film is most preferred since the charge migration of the organic semiconductor may not be inhibited by the binder.

Taking the mechanical strength of the thin film into consideration, a polymer binder having a high glass transition temperature is preferred, and taking the charge mobility into consideration, a polymer binder having a structure that contains no polar group, a photoconductive polymer, and an electroconductive polymer are preferred.

The amount of the polymer binder used is not particularly limited, and the polymer binder may be preferably used in a range of from 0 to 95% by mass, more preferably used in a range of from 10 to 90% by mass, further preferably used in a range of from 20 to 80% by mass, and particularly preferably used in a range of from 30 to 70% by mass, in the organic semiconductor thin film for a non-light emitting organic semiconductor device of the invention.

In the invention, an organic thin film having good film quality may be obtained by using the compound having the aforementioned structure. Specifically, the compound of the invention has good crystallinity to enable formation of a film having a sufficient thickness, and thus the organic semiconductor thin film for a non-light emitting organic semiconductor device of the invention thus obtained may have good quality.

Film Forming Method

The compound of the invention may be formed as a film on a substrate by any method.

On forming the film, the substrate may be heated or cooled, and the film quality and the molecular packing in the film may be controlled by changing the temperature of the substrate. The temperature of the substrate is not particularly limited, and is preferably in a range of from 0 to 200° C., more preferably in a range of from 15 to 100° C., and particularly preferably in a range of from 20 to 95° C.

On forming a film of the compound of the invention on a substrate, the film may be formed by a vacuum process or a solution process, both of which are preferred.

Specific examples of the film formation by a vacuum process include a physical vapor phase growing method, such as a vacuum vapor deposition method, a sputtering method, an ion plating method and a molecular beam epitaxy (MBE) method, and a chemical vapor deposition (CVD) method, such as plasma polymerization, and a vacuum vapor deposition method is preferably used.

The film formation by a solution process means a method, in which an organic compound is dissolved in a solvent capable of dissolving the same, and a film is formed by using the resulting solution. Specific examples thereof used include ordinary methods, for example, a coating method, such as a casting method, a dip coating method, a die coater method, a roll coater method, a bar coater method and a spin coating method, a printing method, such as an ink-jet method, a screen printing method, a gravure printing method, a flexography printing method, an offset printing method and a microcontact printing method, and a Langmuir-Blodgett (LB) method, and a casting method, a spin coating method, an ink-jet method, a gravure printing method, a flexography printing method, an offset printing method and a microcontact printing method are particularly preferably used.

The organic semiconductor thin film for a non-light emitting organic semiconductor device of the invention is preferably produced by a solution coating method. In the case where the organic semiconductor thin film for a non-light emitting organic semiconductor device of the invention contains a polymer binder, the thin film is preferably formed such a method that the material for forming the layer and the polymer binder are dissolved or dispersed in a suitable solvent to prepare a coating liquid, which is then coated by various coating methods to form the thin film.

The coating solution for a non-light emitting organic semiconductor device of the invention capable of being used for film formation by a solution process will be described below.

Coating Solution for Non-Light Emitting Organic Semiconductor Device

The invention also relates to a coating solution for a non-light emitting organic semiconductor device containing the compound represented by the formula (1), i.e., the compound of the invention.

In the case where the film is formed on a substrate by a solution process, the material for forming the layer may be dissolved or dispersed in a suitable organic solvent (for example, a hydrocarbon solvent, such as hexane, octane, decane, toluene, xylene, mesitylene, ethylbenzene, decalin and 1-methylnaphthalene, a ketone solvent, such as acetone, methyl ethyl ketone, methyl isobutyl ketone and cyclohexanone, a halogenated hydrocarbon solvent, such as dichloromethane, chloroform, tetrachloromethane, dichloroethane, trichloroethane, tetrachloroethane, chlorobenzene, dichlorobenzene and chlorotoluene, an ester solvent, such as ethyl acetate, butyl acetate and amyl acetate, an alcohol solvent, such as methanol, propanol, butanol, pentanol, hexanol, cyclohexanol, methyl cellosolve, ethyl cellosolve and ethylene glycol, an ether solvent, such as dibutyl ether, tetrahydrofuran, dioxane and anisole, an amide or imide solvent, such as N,N-dimethylformamide, N,N-dimethylacetamide, 1-methyl-2-pyrrolidone and 1-methyl-2-imidazolidinone, a sulfoxide solvent, such as dimethylsulfoxide, and a nitrile solvent, such as acetonitrile) and/or water to prepare a coating liquid, which may be then coated by various coating methods to form the thin film. The solvent may be used solely or as a combination of plural kinds thereof. Among these, a hydrocarbon solvent, a halogenated hydrocarbon solvent and an ether solvent are preferred, toluene, xylene, mesitylene, tetralin, dichlorobenzene and anisole are more preferred, and toluene, xylene, tetralin and anisole are particularly preferred. The concentration of the compound represented by the formula (1) in the coating liquid is preferably from 0.1 to 80% by mass, more preferably from 0.1 to 10% by mass, and particularly preferably from 0.5 to 10% by mass, by which a film having an arbitrary thickness may be formed.

For forming a film by a solution process, it is necessary to dissolve the materials in the aforementioned solvent, but it is insufficient that the materials are simply dissolved in the solvent. In general, a material to be formed into a film by a vacuum process may be dissolved in a solvent in a certain extent. However, the solution process includes a step of evaporating the solvent to form a thin film, after coating the materials dissolved in a solvent, and most of materials that are not suitable for forming a film by a solution process have high crystallinity, and thus may be disadvantageously crystallized (agglomerated) in the step to fail to provide a favorable thin film. The compound represented by the formula (1) is advantageous also in such a point that the compound may not cause the disadvantageous crystallization (agglomeration).

As the coating solution for a non-light emitting organic semiconductor device of the invention, such an embodiment is also preferred that contains the compound represented by the formula (1), i.e., the compound of the invention, and contains no polymer binder.

The coating solution for a non-light emitting organic semiconductor device of the invention may contain the compound represented by the formula (1), i.e., the compound of the invention, and a polymer binder. In this case, the thin film may be formed in such a manner that the material for forming the layer and the polymer binder are dissolved or dispersed in the suitable solvent described above to prepare a coating liquid, which is then coated by various coating method to form the thin film. The polymer binder may be selected from those described above.

EXAMPLE

The features of the invention will be described more specifically with reference to examples and comparative examples below. The materials, the amounts used, the ratios, the contents of processes, the procedures of processes, and the like shown in the examples may be appropriately changed unless they deviate the substance of the invention. Accordingly, the scope of the invention is not construed as being limited to the following examples.

Example 1

Synthesis Example 1

Synthesis of Compound 5

The compound 5 as the compound represented by the formula (1) was synthesized by the specific synthesis procedures shown by the following scheme. In the following scheme, Tf represents a trifluoromethanesulfonyl group (a triflyl group).

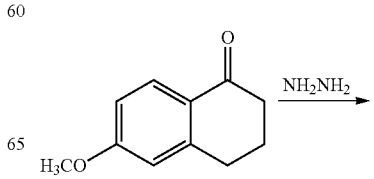

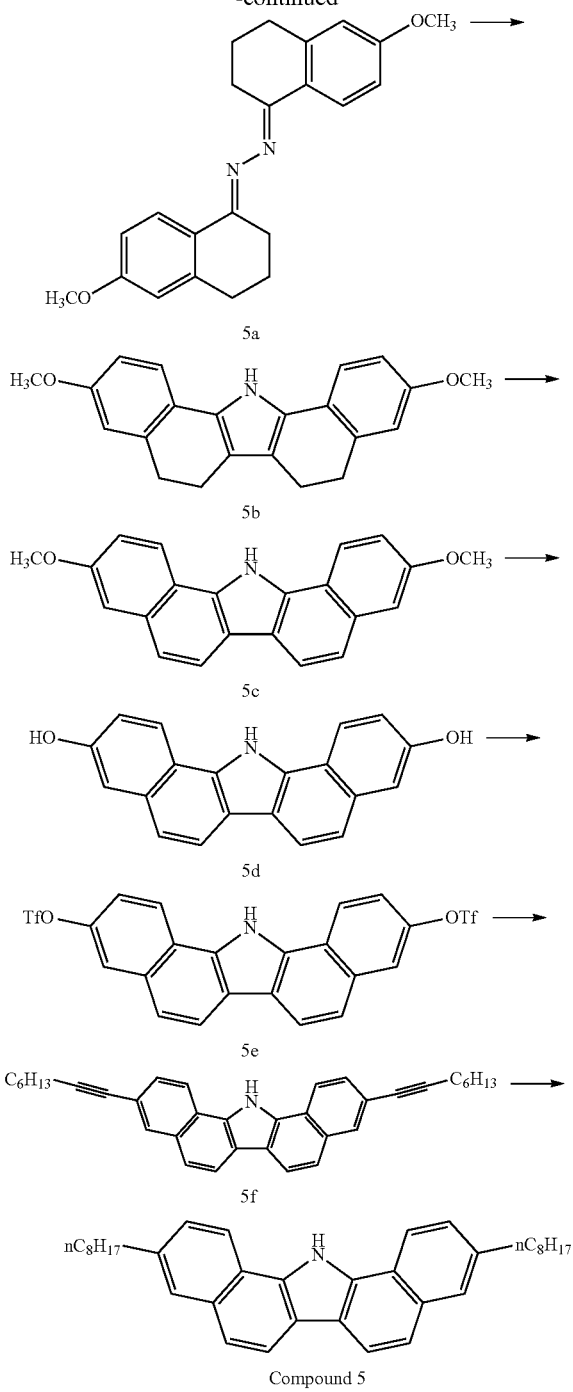

5a

5b

5c

5d

5e

5f

Compound 5

Synthesis of Compound 5a 0.5 mL of concentrated hydrochloric acid was added to 3,4-dihydro-6-methoxynaphthalen-1(2H)-one (25 g) (produced by Wako Pure Chemical Industries, Ltd.) and an ethanol solution (120 mL) of hydrazine monohydrate (4.8 g), and the mixture was stirred under heating to reflux for 4 hours. The solid matter thus deposited was collected by filtration, rinsed with ethanol, and then dried under reduced pressure to provide a compound 5a (18.6 g).

Synthesis of Compound 5b

HCl-containing acetic acid (60 mL) (produced by Sigma-Aldrich Corporation) and acetic anhydride (6 mL) were stirred in a nitrogen atmosphere at 60° C. for 2 hours, to which the compound 5a (15 g) was added, and the mixture was stirred at 120° C. for 2 days. The reaction liquid was poured into a mixture of ethyl acetate and water (1/1), which were then separated into an organic layer and an aqueous layer. The organic layer was washed with a sodium chloride aqueous solution, dried over magnesium sulfate, and then concentrated under reduced pressure. The residue after the concentration was purified by silica gel column chromatography to provide a compound 5b (7.8 g).

Synthesis of Compound 5c

The compound 5b (7.0 g) and a triglyme solution (500 mL) of 10% Pd/C (15 g) were stirred at 190° C. for 4 hours. The reaction liquid was filtered with Celite, and the resulting filtrate was poured into a mixture of toluene and water (1/1), which were then separated into an organic layer and an aqueous layer. The organic layer was washed with water, dried over magnesium sulfate, and then concentrated under reduced pressure. The residue after the concentration was purified by recrystallization from ethyl acetate and hexane to provide a compound 5c (4.3 g).

Synthesis of Compound 5d

A 1M BBr$_3$ methylene chloride solution under cooling with ice was added dropwise to a chloroform solution (62 mL) of the compound 5c (2.1 g), and the mixture was stirred under heating to reflux for 2 hours. The reaction liquid was poured into water, to which ethyl acetate was added, which were then separated into an organic layer and an aqueous layer. The organic layer was washed with a sodium chloride aqueous solution, dried over magnesium sulfate, and then concentrated under reduced pressure to provide a compound 5d (1.5 g).

Synthesis of Compound 5e

Trifluoromethanesulfonic anhydride (2.2 mL) under cooling with ice was added dropwise to a dehydrated pyridine solution (27 mL) of the compound 5d (1.3 g), and the mixture was stirred in a nitrogen atmosphere at room temperature for 1.5 hours. The reaction liquid was poured into a mixture of 1N hydrochloric acid aqueous solution and ethyl acetate (1/1), which were then separated into an organic layer and an aqueous layer. The organic layer was washed with a sodium chloride aqueous solution, dried over magnesium sulfate, and then concentrated under reduced pressure. The residue after the concentration was purified by silica gel column chromatography to provide a compound 5e (2.4 g).

Synthesis of Compound 5f

The compound 5e (1.5 g), 1-octine (2.3 g), PdCl$_2$(PPh$_3$)$_2$ (0.37 g) and a piperidine solution (25 mL) of copper iodide (0.21 g) were stirred in a nitrogen atmosphere at 100° C. for 2 hours. The reaction liquid was poured into a mixture of 1N hydrochloric acid aqueous solution and ethyl acetate (1/1), which were then separated into an organic layer and an aqueous layer. The organic layer was washed with a sodium chloride aqueous solution, dried over magnesium sulfate, and then concentrated under reduced pressure. The residue after the concentration was purified by silica gel column chromatography to provide a compound 5f (1.2 g). The structure of the compound 5f was identified by ¹H-NMR. The compound 5f corresponds to the compound 13 of the invention.

¹H-NMR (CDCl₃): 8.17 (d, 2H), 8.15 (d, 2H), 8.09 (s, 2H), 7.63 (dd, 4H), 2.49 (4H, t), 1.67 (4H, m), 1.51 (4H, m), 1.40-1.27 (12H, m), 0.90 (6H, t)

Synthesis of Compound

10% Pd/C (0.1 g) was added to an isopropyl alcohol solution of the compound 5f (1.0 g), and the mixture was stirred in an autoclave under a hydrogen pressure of 5 kPa at 50° C. for 2 hours. The reaction liquid was filtered with Celite, and the filtrate was concentrated under reduced pressure. The residue after the concentration was purified by silica gel column chromatography to provide the compound 5 (0.9 g). The compound was identified by elemental analysis, NMR and mass spectrum.

The other compounds represented by the formula (1) were synthesized in the similar manner as for the compound 5. The compounds were identified by elemental analysis, NMR and mass spectrum.

The result of the identification of the structure of the compound 11 by ¹H-NMR is shown below.

¹H-NMR (CDCl₃): 8.17 (d, 2H), 8.15 (d, 2H), 8.09 (s, 2H), 7.63 (dd, 4H), 2.49 (4H, t), 1.67 (4H, m), 1.51 (4H, m), 1.15 (6H, t)

Figure 3:
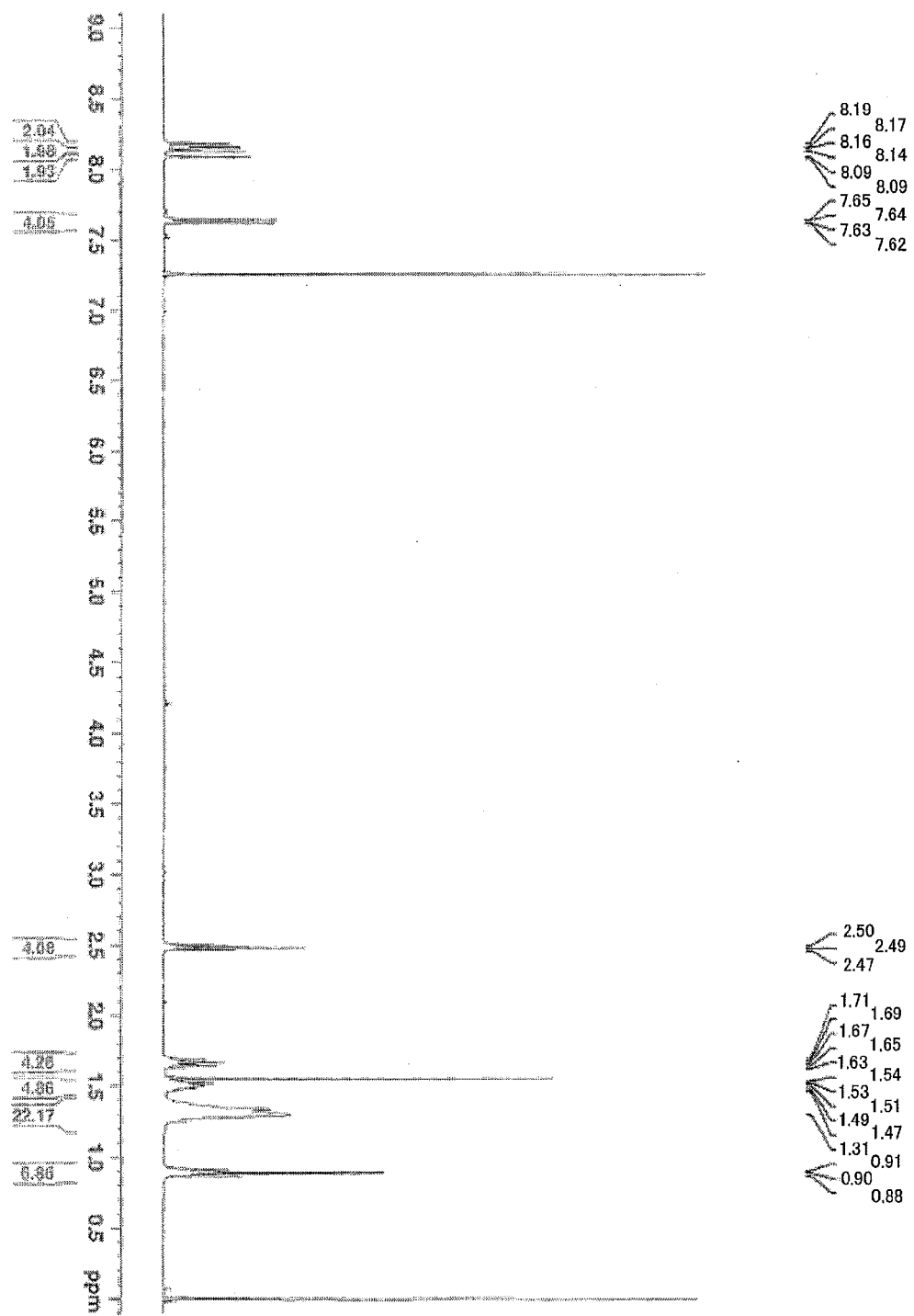
FIG. 3 shows the $^1$H-NMR chart of the compound 47.

The result of the identification of the structure of the compound 47 by ¹H-NMR is shown below and in FIG. 3.

¹H-NMR (CDCl₃): 8.17 (d, 2H), 8.15 (d, 2H), 8.09 (s, 2H), 7.63 (dd, 4H), 2.49 (4H, t), 1.67 (4H, m), 1.51 (4H, m), 1.40-1.27 (24H, m), 0.90 (6H, t)

Comparative compounds 1 to 5 used in a semiconductor active layer (organic semiconductor layer) of comparative devices were synthesized according to the methods described in the literatures. The structures of the comparative compounds 1 to 5 are shown below.

Comparative Compound 1

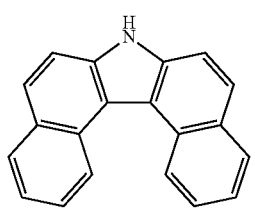

described in
JP-A-2012-513459

Comparative Compound 2

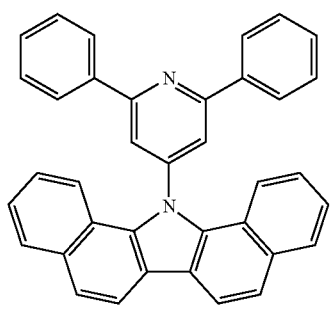

described in
WO 2010/114264

Comparative Compound 2

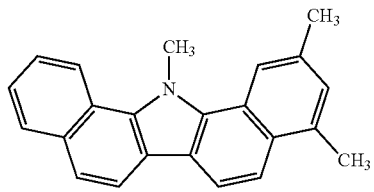

described in
J. Org. Chem. (1950), 15, 950-6

Comparative Compound 4

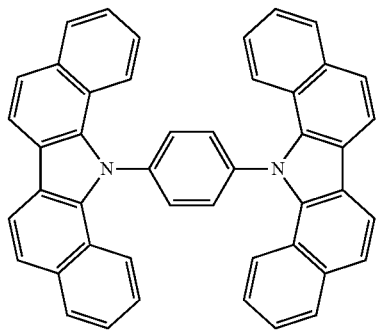

described in
WO 2003/059014

Comparative Compound 5

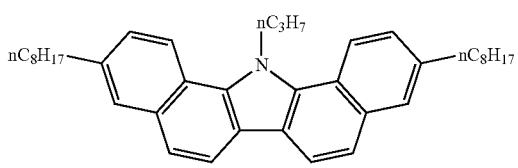

Production and Evaluation of Devices

All the materials used for producing devices were purified by sublimation, and were confirmed to have a purity (absorption intensity area ratio at 254 nm) of 99.5% or more by high-performance liquid chromatography (TSKgel ODS-100Z, available from Tosoh Corporation).

Example 2

Formation of Semiconductor Active Layer (Organic Semiconductor Layer) Only with Compound The compound of the invention or the comparative compound (1 mg each) and toluene (1 mL) were mixed and heated to 100° C. to prepare a coating solution for a non-light emitting organic semiconductor device. The coating solution was cast on a substrate for measuring FET characteristics heated to 90° C. to form an organic semiconductor thin film for a non-light emitting organic semiconductor device, thereby providing an organic thin film transistor device of Example 2 for measuring FET characteristics. The substrate for measuring FET characteristics used was a silicon substrate having a bottom-gate bottom-contact structure having chromium/gold electrodes (gate width W=100 mm, gate length L=100 μm) disposed in an interdigitated form as source and drain electrodes, and SiO₂ (thickness: 200 nm) as an insulating film (the schematic structural illustration shown in FIG. 2).

The FET characteristics of the organic thin film transistor device of Example 2 were evaluated in terms of the carrier mobility and the change in the threshold voltage after repeated driving by using a semiconductor parameter analyzer (4156C, produced by Agilent Technologies, Inc.) having a semi-automatic prober (AX-2000, produced by Vector Semiconductor Co., Ltd.) connected thereto under a normal pressure nitrogen atmosphere.

The results obtained are shown in Table 1 below.

(a) Carrier Mobility

While applying a voltage of −80 V between the source electrode and the drain electrode of the organic thin film (c) Molecular Length of Substituent Z The molecular length of the substituent Z means the length of from the N atom in the N—Z bond in carbazole of the dibenzocarbazole structure to the end of the substituent represented by Z. The structure optimization calculation may be performed by the density functional approach (Gaussian 03 (Gaussian, Inc., U.S.), base function: 6-31G*, exchange correlation function: B3LYP/LANL2DZ).

TABLE 1

| Device No. | Organic semiconductor material | Length of substituent Z | Carrier mobility (cm²/Vs) | Change in threshold voltage after repeated driving | Note |
|---|---|---|---|---|---|
| Device 1 | Compound 1 | 1.0 Å | $3 \times 10^{-1}$ | A | invention |
| Device 2 | Compound 2 | 2.1 Å | $2 \times 10^{-2}$ | A | invention |
| Device 3 | Compound 4 | 3.5 Å | $6 \times 10^{-3}$ | A | invention |
| Device 4 | Compound 5 | 1.0 Å | $6 \times 10^{-1}$ | A | invention |
| Device 5 | Compound 9 | 1.0 Å | $8 \times 10^{-2}$ | A | invention |
| Device 6 | Compound 11 | 1.0 Å | $7 \times 10^{-1}$ | A | invention |
| Device 7 | Compound 13 | 1.0 Å | $4 \times 10^{-1}$ | A | invention |
| Device 8 | Compound 14 | 1.0 Å | $8 \times 10^{-3}$ | A | invention |
| Device 9 | Compound 21 | 1.0 Å | $9 \times 10^{-2}$ | A | invention |
| Device 10 | Compound 26 | 1.0 Å | $4 \times 10^{-2}$ | A | invention |
| Device 11 | Compound 31 | 1.0 Å | $4 \times 10^{-3}$ | A | invention |
| Device 12 | Compound 34 | 1.0 Å | $8 \times 10^{-2}$ | A | invention |
| Device 13 | Compound 36 | 1.0 Å | $6 \times 10^{-2}$ | A | invention |
| Device 14 | Compound 37 | 1.0 Å | $5 \times 10^{-3}$ | A | invention |
| Device 15 | Compound 41 | 1.0 Å | $7 \times 10^{-2}$ | A | invention |
| Device 16 | Compound 43 | 1.0 Å | $1 \times 10^{-1}$ | A | invention |
| Comparative Device 1 | Comparative Compound 1 | 1.0 Å | $1 \times 10^{-3}$ | C | comparison |
| Comparative Device 2 | Comparative Compound 2 | 8.5 Å | $<1 \times 10^{-5}$ | — | comparison |
| Comparative Device 3 | Comparative Compound 3 | 2.1 Å | $7 \times 10^{-4}$ | C | comparison |
| Comparative Device 4 | Comparative Compound 4 | 10.0 Å | $<1 \times 10^{-5}$ | — | comparison |
| Comparative Device 5 | Comparative Compound 5 | 4.6 Å | $6 \times 10^{-5}$ | A | comparison | transistor device (FET device), the gate voltage was changed within a range of from 20 to −100 V, and the carrier mobility μ was calculated by the following expression showing the drain current $I_d$.

$$I_d = (W/2L)\mu C_i (V_g - V_{th})^2$$

wherein L represents the gate length, W represents the gate width, $C_i$ represents the capacity of the insulating layer per unit area, $V_g$ represents the gate voltage, and $V_{th}$ represents the threshold voltage. A device that exhibited a carrier mobility of less than $1 \times 10^{-5}$ cm²/Vs was not subjected to the subsequent evaluation of (b) the change in the threshold voltage after repeated driving due to the too low property thereof.

(b) Change in Threshold Voltage after Repeated Driving

While applying a voltage of −80 V between the source electrode and the drain electrode of the organic thin film transistor device (FET device), the gate voltage was changed 100 times within a range of from 20 to −100 V, and the same measurement as in the measurement (a) above to evaluate the difference ($|V_1-V_0|$) between the threshold voltage $V_0$ before repeated driving and the threshold voltage $V_1$ after repeated driving according to the following three grades. A smaller value thereof shows higher repeated driving stability of the device and thus is preferred.

$|V_1-V_0| \leq 5$ V　　A:

$5 V < |V_1-V_0| \leq 10$ V　　B:

$|V_1-V_0| > 10$ V　　C:

It was understood from Table 1 that the organic thin film transistor devices using the compounds of the invention had a high carrier mobility and a small change in the threshold voltage after repeated driving. Accordingly, it was understood that the compound of the invention was favorably used as an organic semiconductor material for a non-light emitting organic semiconductor device.

On the other hand, the organic thin film transistor devices using the comparative compounds 2 to 5 had a low carrier mobility. The organic thin film transistor devices using the comparative compounds 1 and 3 had a large change in the threshold voltage after repeated driving.

Example 3

Formation of Semiconductor Active Layer (Organic Semiconductor Layer) with Both Compound and Binder Organic thin film transistor devices for measuring FET characteristics were produced in the same manner as in Example 2 except for using a coating solution prepared in such a manner that the compound of the invention or the comparative compound (1 mg each), 1 mg of PαMS (poly (α-methylstyrene), Mw: 300,000, produced by Sigma-Aldrich, Inc.) and toluene (1 mL) were mixed and heated to 100° C., and then evaluated in the same manner as in Example 2.

The results obtained are shown in Table 2 below.

TABLE 2

| Device No. | Organic semiconductor material | Carrier mobility (cm$^2$/Vs) | Change in threshold voltage after repeated driving | Note |
|---|---|---|---|---|
| Device 17 | Compound 1 | $1 \times 10^{-1}$ | A | invention |
| Device 18 | Compound 5 | $3 \times 10^{-1}$ | A | invention |
| Device 19 | Compound 8 | $4 \times 10^{-1}$ | A | invention |
| Device 20 | Compound 10 | $6 \times 10^{-2}$ | A | invention |
| Device 21 | Compound 11 | $3 \times 10^{-1}$ | A | invention |
| Device 22 | Compound 13 | $1 \times 10^{-1}$ | A | invention |
| Device 23 | Compound 14 | $5 \times 10^{-3}$ | A | invention |
| Device 24 | Compound 21 | $4 \times 10^{-2}$ | A | invention |
| Device 25 | Compound 26 | $2 \times 10^{-2}$ | A | invention |
| Device 26 | Compound 43 | $6 \times 10^{-2}$ | A | invention |
| Comparative device 6 | Comparative compound 1 | $3 \times 10^{-4}$ | C | comparison |
| Comparative device 7 | Comparative compound 2 | $<1 \times 10^{-5}$ | — | comparison |
| Comparative device 8 | Comparative compound 3 | $3 \times 10^{-4}$ | C | comparison |
| Comparative device 9 | Comparative compound 4 | $<1 \times 10^{-5}$ | — | comparison |
| Comparative device 10 | Comparative compound 5 | $2 \times 10^{-5}$ | A | comparison |

It was understood from Table 2 that the organic thin film transistor devices having a semiconductor active layer formed by using the compounds of the invention along with the binder had a high carrier mobility and a small change in the threshold voltage after repeated driving. Accordingly, it was understood that the compound of the invention was favorably used as an organic semiconductor material for a non-light emitting organic semiconductor device.

On the other hand, the organic thin film transistor devices having a semiconductor active layer formed by using the comparative compounds 1 to 5 along with the binder had a low carrier mobility. The organic thin film transistor devices having a semiconductor active layer formed by using the comparative compounds 1 and 3 along with the binder had a large change in the threshold voltage after repeated driving.

It was understood from the observation with an optical microscope of the organic thin film transistor devices obtained in Example 3 that the thin films using PαMS as a binder all had considerably high smoothness and uniformity of the film.

It was understood from these results that the comparative devices having a semiconductor active layer formed with the composite system of the binder and the comparative compound had a considerably low carrier mobility, whereas the organic thin film transistor devices of the invention having a semiconductor active layer formed with both the compound of the invention and the binder had a good carrier mobility, a small change in the threshold voltage after repeated driving, and considerably high smoothness and uniformity of the film.

Example 4

Formation of Semiconductor Active Layer (Organic Semiconductor Layer)

A silicon wafer having a gate insulating film of SiO$_2$ (thickness: 370 nm) was subjected to a surface treatment with octyltrichlorosilane.

The compound of the invention or the comparative compound (1 mg each) and toluene (1 mL) were mixed and heated to 100° C. to prepare a coating solution for a non-light emitting organic semiconductor device. The coating solution was cast on the octyltrichlorosilane-treated silicon wafer heated to 90° C. under nitrogen atmosphere to form an organic semiconductor thin film for a non-light emitting organic semiconductor device.

On the surface of the thin film thus formed, gold was vapor-deposited through a mask to form source and drain electrodes, thereby providing an organic thin film transistor device having a bottom-gate top-contact structure having a gate width W of 5 mm and a gate length L of 80 μm (the schematic structural illustration shown in FIG. 1).

The FET characteristics of the organic thin film transistor device of Example 4 were evaluated in terms of the carrier mobility and the change in the threshold voltage after repeated driving by using a semiconductor parameter analyzer (4156C, produced by Agilent Technologies, Inc.) having a semi-automatic prober (AX-2000, produced by Vector Semiconductor Co., Ltd.) connected thereto under a normal pressure nitrogen atmosphere.

The results obtained are shown in Table 3 below.

TABLE 3

| Device No. | Organic semiconductor material | Carrier mobility (cm$^2$/Vs) | Change in threshold voltage after repeated driving | Note |
|---|---|---|---|---|
| Device 27 | Compound 1 | $8 \times 10^{-1}$ | A | invention |
| Device 28 | Compound 2 | $9 \times 10^{-2}$ | A | invention |
| Device 29 | Compound 4 | $4 \times 10^{-2}$ | A | invention |
| Device 30 | Compound 5 | 1.1 | A | invention |
| Device 31 | Compound 6 | $4 \times 10^{-1}$ | A | invention |
| Device 32 | Compound 8 | 1.3 | A | invention |
| Device 33 | Compound 9 | $4 \times 10^{-1}$ | A | invention |
| Device 34 | Compound 11 | 1.2 | A | invention |
| Device 35 | Compound 13 | $9 \times 10^{-1}$ | A | invention |
| Device 36 | Compound 21 | $7 \times 10^{-1}$ | A | invention |
| Device 37 | Compound 26 | $8 \times 10^{-2}$ | A | invention |
| Device 38 | Compound 34 | $4 \times 10^{-1}$ | A | invention |
| Device 39 | Compound 36 | $3 \times 10^{-1}$ | A | invention |
| Device 40 | Compound 39 | $4 \times 10^{-2}$ | A | invention |
| Device 41 | Compound 40 | $2 \times 10^{-2}$ | A | invention |
| Comparative device 11 | Comparative Compound 1 | $6 \times 10^{-3}$ | C | comparison |
| Comparative device 12 | Comparative Compound 2 | $<1 \times 10^{-5}$ | — | comparison |
| Comparative device 13 | Comparative Compound 3 | $3 \times 10^{-3}$ | C | comparison |
| Comparative device 14 | Comparative Compound 4 | $<1 \times 10^{-5}$ | — | comparison |
| Comparative device 15 | Comparative Compound 5 | $4 \times 10^{-4}$ | A | comparison |

It was understood from Table 3 that the organic thin film transistor devices using the compounds of the invention had a high carrier mobility and a small change in the threshold voltage after repeated driving. Accordingly, it was understood that the compound of the invention was favorably used as an organic semiconductor material for a non-light emitting organic semiconductor device.

On the other hand, the organic thin film transistor devices using the comparative compounds 2, 4 and 5 had a low carrier mobility. The organic thin film transistor devices using the comparative compounds 1 and 3 had a large change in the threshold voltage after repeated driving.

While the present invention has been described in detail and with reference to specific embodiments thereof, it will be apparent to one skilled in the art that various changes and modifications can be made therein without departing from the spirit and scope thereof.

The present disclosure relates to the subject matter contained in International Application No. PCT/JP2014/052217 filed on Jan. 31, 2014; Japanese Patent Application No. 2013-017018 filed on Jan. 31, 2013; and Japanese Patent Application No. 2014-015379 filed on Jan. 30, 2014, the contents of which are expressly incorporated herein by reference in their entirety. All the publications referred to in the present specification are also expressly incorporated herein by reference in their entirety.

The foregoing description of preferred embodiments of the invention has been presented for purposes of illustration and description, and is not intended to be exhaustive or to limit the invention to the precise form disclosed. The description was selected to best explain the principles of the invention and their practical application to enable others skilled in the art to best utilize the invention in various embodiments and various modifications as are suited to the particular use contemplated. It is intended that the scope of the invention not be limited by the specification, but be defined claims.

What is claimed is:

1. An organic thin film transistor containing a compound represented by the following formula (1) in a semiconductor active layer:

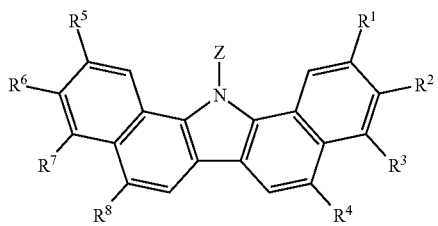

Formula (1)

wherein in the formula (1), Z represents a substituent that has a length of 3.7 Å or less from the N atom to the end of the substituent; each of $R^4$ and $R^8$ represents a hydrogen atom; and $R^1$ to $R^3$ and $R^5$ to $R^7$ each independently represents a hydrogen atom or a substituent, provided that at least one of $R^1$ to $R^3$ and $R^5$ to $R^7$ represents a substituent represented by the following formula (W):

-L-R                     Formula (W)

wherein in the formula (W), L represents a divalent linking group represented by any one of the following formulae (L-1) to (L-4), (L-10), and (L-12), or a divalent linking group containing 2 or more divalent linking groups each represented by any one of the following formulae (L-1) to (L-4), (L-10), and (L-12) bonded to each other; and R represents a substituted or unsubstituted alkyl group having 2 or more carbon atoms, an oligooxyethylene group having a repeating number of an oxyethylene unit of 2 or more, or an oligosiloxane group having 2 or more silicon atoms:

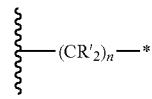

(L-1)

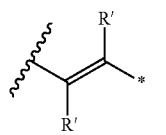

(L-2)

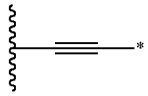

(L-3)

(L-4)

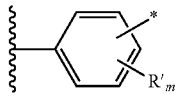

(L-10)

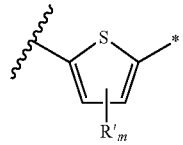

(L-12)

wherein in the formulae (L-1) to (L-4), (L-10), and (L-12), the wavy line represents a position bonded to the dibenzocarbazole skeleton, and * represents a position bonded to R in the formula (W); in the formula (L-1), n represents an integer of 1 or more; in the formula (L-10), m represents 4; in the formula (L-12), m represents 2; and in the formulae (L-1), (L-2), (L-10), and (L-12), R' each independently represent a hydrogen atom or a substituent, wherein in the formula (1), Z represents a hydrogen atom, a methyl group, or a methyl group substituted by a cyano group.

2. The organic thin film transistor according to claim 1, wherein at least one of $R^2$, $R^3$, $R^6$ and $R^7$ represents a substituent represented by the formula (W).

3. The organic thin film transistor according to claim 1, wherein the compound represented by the formula (1) is a compound represented by the following formula (2-1) or (2-2):

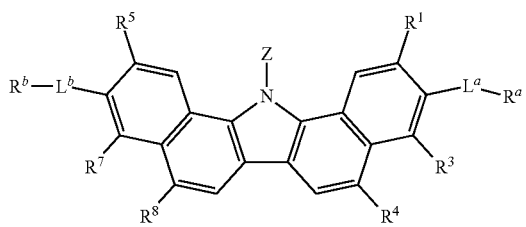

Formula (2-1)

wherein in the formula (2-1), each of $R^4$ and $R^8$ represents a hydrogen atom; $R^1$, $R^3$, $R^5$, and $R^7$ each independently represent a hydrogen atom or a substituent; $L^a$ and $L^b$ each independently represent a divalent linking group represented by any one of the following formulae (L-1) to (L-4), (L-10), and (L-12), or a divalent linking group containing 2 or more divalent linking groups each represented by any one of the following formulae (L-1) to (L-4), (L-10), and (L-12) bonded to each other; and $R^a$ and $R^b$ each independently represent a substituted or unsubstituted alkyl group having 2 or more carbon atoms, an oligooxyethylene group having a repeating number of an oxyethylene unit of 2 or more, or an oligosiloxane group having 2 or more silicon atoms, Formula (2-2)

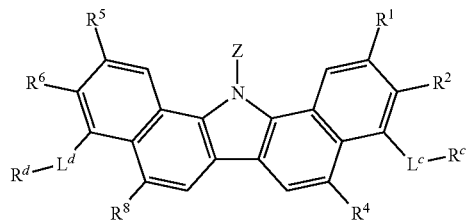

wherein in the formula (2-2), each of $R^4$ and $R^8$ represents a hydrogen atom; $R^1$, $R^2$, $R^5$ and $R^6$, each independently represent a hydrogen atom or a substituent; $L^c$ and $L^d$ each independently represent a divalent linking group represented by any one of the following formulae (L-1) to (L-4), (L-10), and (L-12), or a divalent linking group containing 2 or more divalent linking groups each represented by any one of the following formulae (L-1) to (L-4), (L-10), and (L-12) bonded to each other; and $R^c$ and $R^d$ each independently represent a substituted or unsubstituted alkyl group having 2 or more carbon atoms, an oligooxyethylene group having a repeating number of an oxyethylene unit of 2 or more, or an oligosiloxane group having 2 or more silicon atoms:

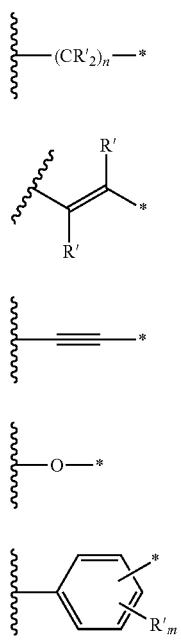

(L-12)

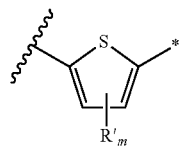

wherein in the formulae (L-1) to (L-4), (L-10), and (L-12) in the formulae (2-1) and (2-2), the wavy line represents a position bonded to the dibenzocarbazole skeleton, and * each independently represents a position bonded to any one of $R^a$, $R^b$, $R^c$ and $R^d$ adjacent to the formulae (L-1) to (L-4), (L-10), and (L-12); in the formula (L-1), n represents an integer of 1 or more; in the formula (L-10), m represents 4; in the formula (L-12), m represents 2; and in the formulae (L-1), (L-2), (L-10), and (L-12), R' each independently represent a hydrogen atom or a substituent.

4. The organic thin film transistor according to claim 3, wherein in the formula (2-1) or (2-2), all of $L^a$, $L^b$, $L^c$ and $L^d$ each represent a divalent linking group represented by any one of the formulae (L-1) to (L-3), (L-10), or (L-12), or a divalent linking group containing 2 or more of the divalent linking groups bonded to each other.

5. The organic thin film transistor according to claim 3, wherein in the formula (2-1) or (2-2), all of $L^a$, $L^b$, $L^c$ and $L^d$ each represent a divalent linking group represented by the formula (L-1) or (L-10).

6. The organic thin film transistor according to claim 3, wherein in the formula (2-1) or (2-2), all $R^a$, $R^b$, $R^c$ and $R^d$ each represent an alkyl group having 2 or more carbon atoms.

7. The organic thin film transistor according to claim 3, wherein in the formula (2-1) or (2-2), all $R^a$, $R^b$, $R^c$ and $R^d$ each represent a linear alkyl group having from 3 to 12 carbon atoms.

8. A compound represented by the following formula (1):

Formula (1)

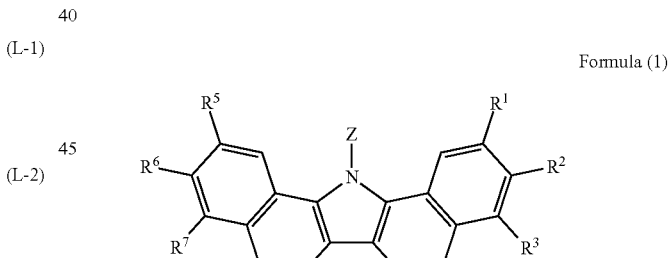

wherein in the formula (1), Z represents a substituent that has a length of 3.7 Å or less from the N atom to the end of the substituent; each of $R^4$ and $R^8$ represents a hydrogen atom; and $R^1$ to $R^3$ and $R^5$ to $R^7$ each independently represents a hydrogen atom or a substituent, provided that at least one of $R^1$ to $R^3$ and $R^5$ to $R^7$ represents a substituent represented by the following formula (W):

-L-R            Formula (W)

wherein in the formula (W), L represents a divalent linking group represented by any one of the following formulae (L-1) to (L-4), (L-10), and (L-12), or a divalent linking group containing 2 or more divalent linking groups each represented by any one of the following formulae (L-1) to (L-4), (L-10), and (L-12) bonded to each other; and R represents a substituted or unsubstituted alkyl group having 2 or more carbon atoms, an oligooxyethylene group having a repeating number of an oxyethylene unit of 2 or more, or an oligosiloxane group having 2 or more silicon atoms:

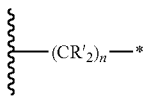
(L-1)

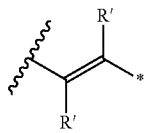
(L-2)

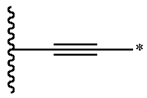
(L-3)

(L-4)

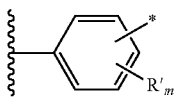
(L-10)

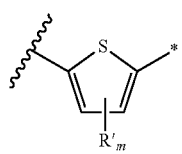
(L-12)

wherein in the formulae (L-1) to (L-4), (L-10), and (L-12), the wavy line represents a position bonded to the dibenzocarbazole skeleton, and * represents a position bonded to R in the formula (W); in the formula (L-1), n represents an integer of 1 or more; in the formula (L-10), m represents 4; in the formula (L-12), m represents 2; and in the formulae (L-1), (L-2), (L-10), and (L-12), R' each independently represent a hydrogen atom or a substituent, wherein in the formula (1), Z represents a hydrogen atom, a methyl group, or a methyl group substituted by a cyano group.

9. The compound according to claim 8, wherein at least one of $R^2$, $R^3$, $R^6$ and $R^7$ represents a substituent represented by the formula (W).

10. The compound according to claim 8, wherein the compound represented by the formula (1) is a compound represented by the following formula (2-1) or (2-2):

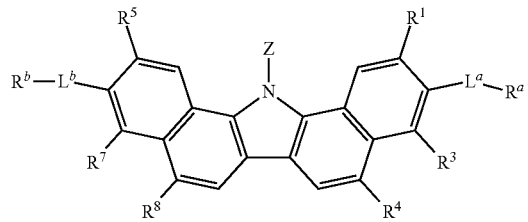
Formula (2-1)

wherein in the formula (2-1), each of $R^4$ and $R^8$ represents a hydrogen atom; $R^1$, $R^3$, $R^5$, and $R^7$ each independently represent a hydrogen atom or a substituent; $L^a$ and $L^b$ each independently represent a divalent linking group represented by any one of the following formulae (L-1) to (L-4), (L-10), and (L-12), or a divalent linking group containing 2 or more divalent linking groups each represented by any one of the following formulae (L-1) to (L-4), (L-10), and (L-12) bonded to each other; and $R^a$ and $R^b$ each independently represent a substituted or unsubstituted alkyl group having 2 or more carbon atoms, an oligooxyethylene group having a repeating number of an oxyethylene unit of 2 or more, or an oligosiloxane group having 2 or more silicon atoms,

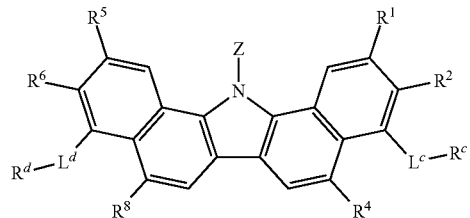
Formula (2-2)

wherein in the formula (2-2), each of $R^4$ and $R^8$ represents a hydrogen atom; $R^1$, $R^2$, $R^5$ and $R^6$, each independently represent a hydrogen atom or a substituent; $L^c$ and $L^d$ each independently represent a divalent linking group represented by any one of the following formulae (L-1) to (L-4), (L-10), and (L-12), or a divalent linking group containing 2 or more divalent linking groups each represented by any one of the following formulae (L-1) to (L-4), (L-10), and (L-12) bonded to each other; and $R^c$ and $R^d$ each independently represent a substituted or unsubstituted alkyl group having 2 or more carbon atoms, an oligooxyethylene group having a repeating number of an oxyethylene unit of 2 or more, or an oligosiloxane group having 2 or more silicon atoms:

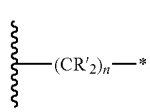
(L-1)

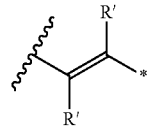
(L-2)

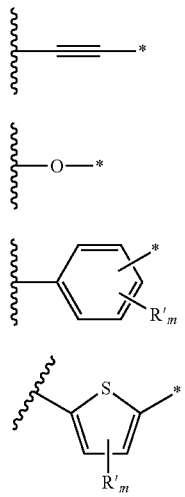

(L-3)

(L-4)

(L-10)

(L-12)

wherein in the formulae (L-1) to (L-4), (L-10), and (L-12) in the formulae (2-1) and (2-2), the wavy line represents a position bonded to the dibenzocarbazole skeleton, and * each independently represents a position bonded to any one of $R^a$, $R^b$, $R^c$ and $R^d$ adjacent to the formulae (L-1) to (L-4), (L-10), and (L-12); in the formula (L-1), n represents an integer of 1 or more; in the formula (L-10), m represents 4; in the formula (L-12), m represents 2; and in the formulae (L-1), (L-2), (L-10), and (L-12), R' each independently represent a hydrogen atom or a substituent.

11. The compound according to claim 10, wherein in the formula (2-1) or (2-2), all of $L^a$, $L^b$, $L^c$ and $L^d$ each represent a divalent linking group represented by any one of the formulae (L-1) to (L-3), (L-10), or (L-12), or a divalent linking group containing 2 or more of the divalent linking groups bonded to each other.

12. The compound according to claim 10, wherein in the formula (2-1) or (2-2), all of $L^a$, $L^b$, $L^c$ and $L^d$ each represent a divalent linking group represented by the formula (L-1) or (L-10).

13. The compound according to claim 10, wherein in the formula (2-1) or (2-2), all $R^a$, $R^b$, $R^c$ and $R^d$ each represent an alkyl group having 2 or more carbon atoms.

14. The compound according to claim 10, wherein in the formula (2-1) or (2-2), all $R^a$, $R^b$, $R^c$ and $R^d$ each represent a linear alkyl group having from 3 to 12 carbon atoms.

15. An organic semiconductor material for a non-light emitting organic semiconductor device, containing a compound represented by the following formula (1):

Formula (1)

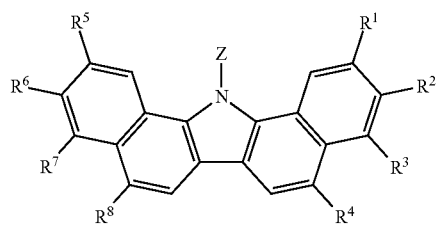

wherein in the formula (1), Z represents a substituent that has a length of 3.7 Å or less from the N atom to the end of the substituent; each of $R^4$ and $R^8$ represents a hydrogen atom; and $R^1$ to $R^3$ and $R^5$ to $R^7$ each independently represents a hydrogen atom or a substituent, provided that at least one of $R^1$ to $R^3$ and $R^5$ to $R^7$ represents a substituent represented by the following formula (W):

-L-R    Formula (W)

wherein in the formula (W), L represents a divalent linking group represented by any one of the following formulae (L-1) to (L-4), (L-10), and (L-12), or a divalent linking group containing 2 or more divalent linking groups each represented by any one of the following formulae (L-1) to (L-4), (L-10), and (L-12) bonded to each other; and R represents a substituted or unsubstituted alkyl group having 2 or more carbon atoms, an oligooxyethylene group having a repeating number of an oxyethylene unit of 2 or more, or an oligosiloxane group having 2 or more silicon atoms:

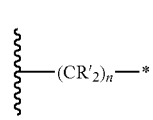
(L-1)

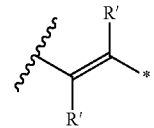
(L-2)

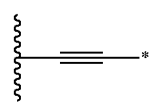
(L-3)

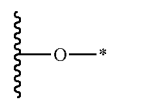
(L-4)

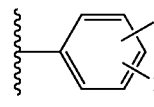
(L-10)

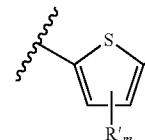
(L-12)

wherein in the formulae (L-1) to (L-4), (L-10), and (L-12), the wavy line represents a position bonded to the dibenzocarbazole skeleton, and * represents a position bonded to R in the formula (W); in the formula (L-1), n represents an integer of 1 or more; in the formula (L-10), m represents 4; in the formula (L-12), m represents 2; and in the formulae (L-1), (L-2), (L-10), and (L-12), R' each independently represent a hydrogen atom or a substituent, wherein in the formula (1), Z represents a hydrogen atom, a methyl group, or a methyl group substituted by a cyano group.

16. A material for an organic thin film transistor, containing a compound represented by the following formula (1):

Formula (1)

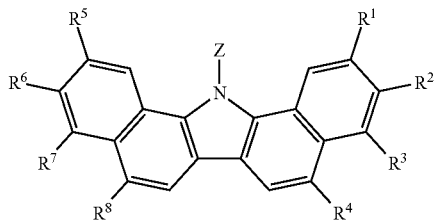

wherein in the formula (1), Z represents a substituent that has a length of 3.7 Å or less from the N atom to the end of the substituent; each of $R^4$ and $R^8$ represents a hydrogen atom; and $R^1$ to $R^3$ and $R^5$ to $R^7$ each independently represents a hydrogen atom or a substituent, provided that at least one of $R^1$ to $R^3$ and $R^5$ to $R^7$ represents a substituent represented by the following formula (W):

-L-R   Formula (W)

wherein in the formula (W), L represents a divalent linking group represented by any one of the following formulae (L-1) to (L-4), (L-10), and (L-12), or a divalent linking group containing 2 or more divalent linking groups each represented by any one of the following formulae (L-1) to (L-4), (L-10), and (L-12) bonded to each other; and R represents a substituted or unsubstituted alkyl group having 2 or more carbon atoms, an oligooxyethylene group having a repeating number of an oxyethylene unit of 2 or more, or an oligosiloxane group having 2 or more silicon atoms:

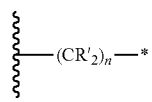
(L-1)

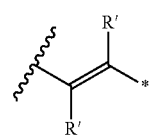
(L-2)

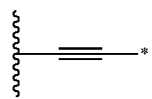
(L-3)

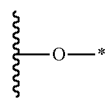
(L-4)

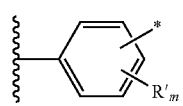
(L-10)

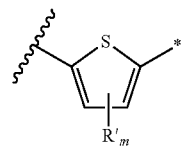
(L-12)

wherein in the formulae (L-1) to (L-4), (L-10), and (L-12), the wavy line represents a position bonded to the dibenzocarbazole skeleton, and * represents a position bonded to R in the formula (W); in the formula (L-1), n represents an integer of 1 or more; in the formula (L-10), m represents 4; in the formula (L-12), m represents 2; and in the formulae (L-1), (L-2), (L-10), and (L-12), R' each independently represent a hydrogen atom or a substituent, wherein in the formula (1), Z represents a hydrogen atom, a methyl group, or a methyl group substituted by a cyano group.

17. A coating solution for a non-light emitting organic semiconductor device, containing a compound represented by the following formula (1):

Formula (1)

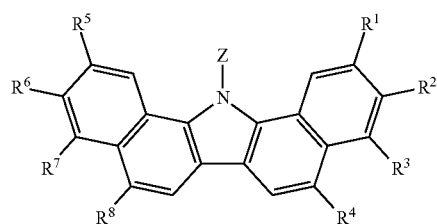

wherein in the formula (1), Z represents a substituent that has a length of 3.7 Å or less from the N atom to the end of the substituent; each of $R^4$ and $R^8$ represents a hydrogen atom; and $R^1$ to $R^3$ and $R^5$ to $R^7$ each independently represents a hydrogen atom or a substituent, provided that at least one of $R^1$ to $R^3$ and $R^5$ to $R^7$ represents a substituent represented by the following formula (W):

-L-R   Formula (W)

wherein in the formula (W), L represents a divalent linking group represented by any one of the following formulae (L-1) to (L-4), (L-10), and (L-12), or a divalent linking group containing 2 or more divalent linking groups each represented by any one of the following formulae (L-1) to (L-4), (L-10), and (L-12) bonded to each other; and R represents a substituted or unsubstituted alkyl group having 2 or more carbon atoms, an oligooxyethylene group having a repeating number of an oxyethylene unit of 2 or more, or an oligosiloxane group having 2 or more silicon atoms:

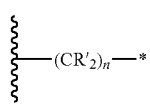
(L-1)

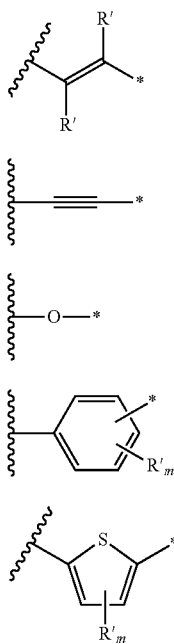

(L-2)

(L-3)

(L-4)

(L-10)

(L-12)

wherein in the formulae (L-1) to (L-4), (L-10), and (L-12), the wavy line represents a position bonded to the dibenzocarbazole skeleton, and * represents a position bonded to R in the formula (W); in the formula (L-1), n represents an integer of 1 or more; in the formula (L-10), m represents 4; in the formula (L-12), m represents 2; and in the formulae (L-1), (L-2), (L-10), and (L-12), R' each independently represent a hydrogen atom or a substituent, wherein in the formula (1), Z represents a hydrogen atom, a methyl group, or a methyl group substituted by a cyano group.

18. The coating solution for a non-light emitting organic semiconductor device according to claim 17, containing the compound represented by the formula (1) and a polymer binder.

19. An organic semiconductor thin film for a non-light emitting organic semiconductor device, containing a compound represented by the following formula (1):

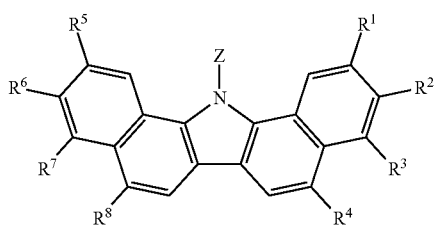

Formula (1)

wherein in the formula (1), Z represents a substituent that has a length of 3.7 Å or less from the N atom to the end of the substituent; each of $R^4$ and $R^8$ represents a hydrogen atom; and $R^1$ to $R^3$ and $R^5$ to $R^7$ each independently represents a hydrogen atom or a substituent, provided that at least one of $R^1$ to $R^3$ and $R^5$ to $R^7$ represents a substituent represented by the following formula (W):

-L-R    Formula (W)

wherein in the formula (W), L represents a divalent linking group represented by any one of the following formulae (L-1) to (L-4), (L-10), and (L-12), or a divalent linking group containing 2 or more divalent linking groups each represented by any one of the following formulae (L-1) to (L-4), (L-10), and (L-12) bonded to each other; and R represents a substituted or unsubstituted alkyl group having 2 or more carbon atoms, an oligooxyethylene group having a repeating number of an oxyethylene unit of 2 or more, or an oligosiloxane group having 2 or more silicon atoms:

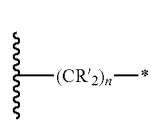

(L-1)

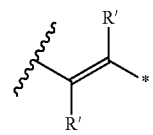

(L-2)

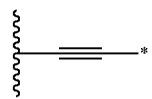

(L-3)

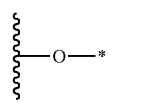

(L-4)

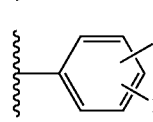

(L-10)

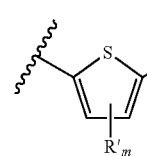

(L-12)

wherein in the formulae (L-1) to (L-4), (L-10), and (L-12), the wavy line represents a position bonded to the dibenzocarbazole skeleton, and * represents a position bonded to R in the formula (W); in the formula (L-1), n represents an integer of 1 or more; in the formula (L-10), m represents 4; in the formula (L-12), m represents 2; and in the formulae (L-1), (L-2), (L-10), and (L-12), R' each independently represent a hydrogen atom or a substituent, wherein in the formula (1), Z represents a hydrogen atom, a methyl group, or a methyl group substituted by a cyano group.

20. The organic semiconductor thin film for a non-light emitting organic semiconductor device according to claim 19, containing the compound represented by the formula (1) and a polymer binder.

21. The organic semiconductor thin film for a non-light emitting organic semiconductor device according to claim 19, which is produced by a solution coating method.

* * * * *